US011786169B2

(12) United States Patent
Evans

(10) Patent No.: US 11,786,169 B2
(45) Date of Patent: Oct. 17, 2023

(54) SYSTEM, APPARATUS, AND METHOD FOR MONITORING AND ASSESSING THE LEVEL OF FETAL RISK DURING LABOR

(71) Applicant: Mark Evans, Las Vegas, NV (US)

(72) Inventor: Mark Evans, Las Vegas, NV (US)

( * ) Notice: Subject to any disclaimer, the term of this patent is extended or adjusted under 35 U.S.C. 154(b) by 0 days.

(21) Appl. No.: 16/348,028

(22) PCT Filed: Nov. 21, 2017

(86) PCT No.: PCT/US2017/062820
§ 371 (c)(1),
(2) Date: May 7, 2019

(87) PCT Pub. No.: WO2018/094398
PCT Pub. Date: May 24, 2018

(65) Prior Publication Data
US 2019/0274618 A1 Sep. 12, 2019

Related U.S. Application Data

(60) Provisional application No. 62/425,018, filed on Nov. 21, 2016.

(51) Int. Cl.
*A61B 5/00* (2006.01)
*A61B 5/024* (2006.01)

(52) U.S. Cl.
CPC ........ *A61B 5/4362* (2013.01); *A61B 5/02411* (2013.01); *A61B 5/4356* (2013.01); *A61B 5/0011* (2013.01)

(58) Field of Classification Search
CPC .............. A61B 5/0011; A61B 5/02405; A61B 5/02411; A61B 5/1107; A61B 5/4356; A61B 5/4362; A61B 2503/02
(Continued)

(56) References Cited

U.S. PATENT DOCUMENTS 3,989,034 A 11/1976 Hojaiban
4,821,732 A 4/1989 Lippes
(Continued)

FOREIGN PATENT DOCUMENTS

CN 103793607 5/2014
CN 104798074 A 7/2015
(Continued)

OTHER PUBLICATIONS

European Patent Office; Extended Search Report Communication pursuant to Rule 62 EPC;dated Jun. 7, 2020, Application No. 17872197.3-1115/3541276 PCT/2017062820, Ref. DD/P275204EP.
(Continued)

*Primary Examiner* — Carl H Layno
*Assistant Examiner* — Jane C Kalinock
(74) *Attorney, Agent, or Firm* — Dickinson Wright PLLC

(57) ABSTRACT

An apparatus has a computer receiving input signals indicative of fetal heart rate ("FHR") and maternal uterine activity in a patient. The computer determines when each of FHR, baseline FHR variability, FHR accelerations, FHR decelerations, and maternal uterine activity exhibit a plurality of pre-defined non-reassuring characteristics. The computer receives inputs indicating the presence of maternal, obstetrical, and fetal risk factors, and determines at predetermined times during labor a present level of risk to the fetus which accounts for the total of the number of parameters that each exhibit the non-reassuring characteristics at predetermined points in time during labor and the number of risk factors present. An output display depicts in a single graphical interface information respecting the parameters and risk factors over time during labor. The graphical interface includes indicia for indicating the present level of fetal risk at the predetermined times during labor and signals the need for intervention.

30 Claims, 8 Drawing Sheets

(58) Field of Classification Search
USPC .......................................................... 600/511
See application file for complete search history.

(56) References Cited

U.S. PATENT DOCUMENTS

| | | | |
|---|---|---|---|
| 4,951,680 A | 8/1990 | Kirk | |
| 5,069,218 A | 12/1991 | Ikeda | |
| 5,088,497 A | 2/1992 | Ikeda | |
| 5,123,420 A | 6/1992 | Paret | |
| 5,425,362 A | 6/1995 | Siker | |
| 5,433,204 A | 7/1995 | Olson | |
| 5,442,940 A | 8/1995 | Secker | |
| 5,474,065 A | 12/1995 | Meathrel | |
| 5,497,317 A | 3/1996 | Hawkins | |
| 5,511,553 A | 4/1996 | Segalowitz | |
| 5,596,993 A | 1/1997 | Oriol | |
| 5,623,939 A | 4/1997 | Garfield | |
| 5,851,188 A | 12/1998 | Bullard | |
| 5,954,663 A | 9/1999 | Gat | |
| 5,957,855 A | 9/1999 | Oriol | |
| 6,024,701 A | 2/2000 | Almog | |
| 6,254,537 B1 | 7/2001 | Nguyen | |
| 6,340,346 B1 | 1/2002 | Almog | |
| 6,423,016 B1 | 7/2002 | Hamilton | |
| 6,434,418 B1 | 8/2002 | Neal | |
| 6,522,916 B1 | 2/2003 | Kwon | |
| 6,751,498 B1 | 6/2004 | Greenberg | |
| 7,113,819 B2 | 9/2006 | Hamilton | |
| 7,313,424 B2 | 12/2007 | Mayevsky | |
| 7,314,451 B2 | 1/2008 | Halperin | |
| 7,333,850 B2 | 2/2008 | Marossero | |
| 7,850,625 B2 | 12/2010 | Paltieli | |
| 9,078,582 B2 | 7/2015 | Tupin, Jr. et al. | |
| 9,131,860 B2 | 9/2015 | Evans | |
| 9,691,983 B2 | 6/2017 | Soga et al. | |
| 10,448,891 B2 | 10/2019 | Amir et al. | |
| 2003/0187364 A1 | 10/2003 | Hamilton | |
| 2004/0100376 A1 | 5/2004 | Lye | |
| 2005/0267377 A1 | 12/2005 | Marossero et al. | |
| 2006/0074329 A1 | 4/2006 | Ferguson | |
| 2007/0213627 A1 | 9/2007 | James | |
| 2007/0233203 A1* | 10/2007 | Euliano | A61B 5/339 607/46 |
| 2007/0255588 A1 | 11/2007 | Hamilton | |
| 2010/0168528 A1* | 7/2010 | Evans | A61B 5/02405 600/301 |
| 2010/0268124 A1 | 10/2010 | Hamilton | |
| 2011/0071414 A1 | 3/2011 | Heil et al. | |
| 2012/0142604 A1 | 6/2012 | Faivre | |
| 2013/0281861 A1* | 10/2013 | Flomerfelt | A61B 8/02 600/483 |
| 2014/0301949 A1 | 10/2014 | Rabi | |
| 2015/0157276 A1 | 6/2015 | Gratacos et al. | |
| 2015/0248534 A1 | 9/2015 | Krzywicki | |
| 2016/0270658 A1 | 9/2016 | Ater | |
| 2017/0308662 A1* | 10/2017 | Hamilton | G16H 40/63 |

FOREIGN PATENT DOCUMENTS

| | | |
|---|---|---|
| EP | 0384339 | 8/1990 |
| EP | 1568316 | 8/2005 |
| JP | 2012524627 | 10/2012 |
| KR | 1020010105460 | 11/2001 |
| WO | WO 98/49942 | 11/1998 |
| WO | WO 00/01117 | 1/2000 |
| WO | WO 2007/120873 | 10/2007 |
| WO | WO2010124117 | 10/2010 |

OTHER PUBLICATIONS

Intermittent Auscultation for Intrapartum Fetal Heart Rate Surveillance; Journal of Midwifery & Women's Health; Mar. 2010; No. 11; pp. 397-403; Elsevier Inc; Silver Spring, MD.
International Search Report, for International Application No. PCT/US2017/62820; dated Jan. 17, 2018.
Written Opinion of the International Searching Authority for International Application No. PCT/US2017/62820; dated Jan. 17, 2018.
Parer et al., "A framework for standardized management of intrapartum fetal heart rate patterns", Am. Jour. Obst. & Gyn., Jul. 2007, p. 26.e1-26.e6.
Parer, JT, "FHR Monitoring: Can we expect improvements soon?", Maternal Fetal Medicine, University of California San Francisco, MFM Fellows Videoconference Series, May 21, 2008.
Yuki Kodama et al., "Intrapartum fetal heart rate patterns in infants with (>-34 weeks) with poor neurological outcome"; Early Human Development 85 (2009), pp. 235-238.
Deidre M. Murray, M.D., et al., Fetal Heart Rate Patterns in Neonatal Hypoxic-Ischemic Encephalopathy: Relationship with Early Cerebral Activity and Neurodevelopmental Outcome; American Journal of Peinatology, vol. 26, No. 8 (2009).

* cited by examiner

SYSTEM, APPARATUS, AND METHOD FOR MONITORING AND ASSESSING THE LEVEL OF FETAL RISK DURING LABOR

CROSS-REFERENCE TO RELATED APPLICATIONS

This application is a Section 371 National Stage of International Application PCT/US2017/062820, filed 21 Nov. 2017, and through which priority is claimed to United States Provisional Application Ser. No. 62/425,018, filed 21 Nov. 2016.

FIELD OF THE INVENTION

The invention pertains to a method and apparatus for identifying the present level of fetal risk during labor by taking into account both electronic fetal monitoring and a number of fetal, obstetric and maternal parameters and transforming those parameters into a corresponding indication of the level of risk to the fetus during labor.

BACKGROUND

It is well-known that when fetal status is compromised, any diminution in maternal cardiac output, oxygenation of the maternal blood, or maternal uterine blood flow will place the fetus at significant subsequent risk for the development of fetal hypoxia and asphyxia (metabolic acidosis) if labor and its sequelae, often including impaired oxygenation, are allowed to continue. It is estimated that, in the United States, 700 infant deaths per year are the result of intrauterine hypoxia and birth asphyxia. It is also widely accepted that fetal neurological injury that develops during labor results from progressive hypoxia and acidemia severe enough to produce cerebral ischemia.

Electronic fetal monitoring (EFM) was introduced in the late 1950's in an attempt to permit timely intervention (e.g., expedited delivery by cesarean section) in situations in which the fetus appears to either be presently compromised already or will be so imminently. EFM has been widely adopted and is currently used in the majority of births in the United States.

The premise of EFM is the recognition of asphyxia related to metabolic acidemia. The response to fetal heart rate (FHR) patterns is predicated on the identification and "rescue" of the asphyxiated fetus, hopefully, before it has suffered damage. Traditionally, when any of the parameters of the FHM data demonstrate "reassurance," labor is allowed to continue, with intervention being reserved for the situation when all of these parameters are abnormal, indicative of significant asphyxia (metabolic acidosis), or an acute emergency arises (e.g., fetal bradycardia). This approach, based on "rescue" of the fetus, has not resulted in improved outcomes either immediately or long-term. Despite obvious beneficial impacts on intrapartum stillbirth, neonatal death rates, and reduction in neonatal seizures, EFM has failed to produce the expected reduction in neonatal encephalopathy and cerebral palsy (NEACP) and long-term handicap rates. With high rates of both intra- and inter-observer error, it has been further criticized as an imprecise, subjective, and poorly predictive measure of fetal well-being with a high false positive rate leading to unnecessary intervention, but without the discriminatory power to identify the truly hypoxic or injured fetus. A number of published classifications and management guidelines have appeared from various sources with no apparent improvement in neurological outcome or reduction in the allegations of obstetrical negligence. Concomitantly, there are world-wide efforts to reduce the cesarean section rate in part by increasing the tolerance for increasing lengths of labor and for abnormal FHR patterns. The safety of these initiatives has been questioned.

The near ubiquitous use of EFM has failed to lower the rate of both cerebral palsy and emergency operative deliveries (EOD). Its performance metrics have low sensitivity, specificity, and predictive values for both. There are many EODs, and the vast majority have normal outcomes. EODs, however, cause serious disruption of the delivery suite routine with increased complications, anxiety, and concern for all.

Accordingly, there continues to exist a need for a more standardized interpretation of labor progress and FHR tracings, and which provides for the quantification of these parameters to objectively identify the level of risk for the subsequent development of adverse outcomes such as fetal hypoxia and acidosis if labor is allowed to continue without intervention.

SUMMARY

The specification discloses a system, method and apparatus for identifying the present level of fetal risk during labor. In one form, the present invention comprehends an apparatus for identifying the level of fetal risk during labor, the apparatus comprising:

At least one computer operative to receive input signals indicative of at least FHR and maternal uterine activity in a patient, the at least one computer further operative (i) to determine from the FHR at least baseline FHR variability, FHR accelerations, and FHR decelerations, and (ii) to determine when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e).

The at least one computer is further operative to (iii) receive user-inputs indicative of the presence in the patient of one or more (f) maternal risk factors, (g) obstetrical risk factors, and (h) fetal risk factors distinct from the parameters (a) through (d) which elevate the level of fetal risk during labor, and (iv) to determine at a given point in time during labor a present level of risk to the fetus which takes into account only: the total number of the parameters (a) through (e) that each simultaneously, independently exhibit at least one of the non-reassuring characteristics at the given point in time during labor, and the total number of the parameters (f) through (h) which are present.

At least one output is operatively connected to the at least one computer, the at least one output comprising a display which continuously depicts in a single graphical user interface one or more of the parameters (a) through (h) over time during labor, and the appearance of which single graphical user interface includes indicia for indicating the determined present level of risk to the fetus at any given point in time during labor and signaling the need for possible intervention in labor.

The method of the present invention comprehends the following:

Monitoring fetal heart rate ("FHR") and maternal uterine activity in a patient;

Determining from the FHR at least: baseline FHR variability, FHR accelerations, and FHR decelerations, and when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e);

Determining the presence in the patient of one or more parameters in the form of (f) maternal risk factors, (g) obstetrical risk factors, and (h) fetal risk factors distinct from the parameters (a) through (d) which elevate the level of fetal risk during labor;

Determining at a given point in time during labor a present level of risk to the fetus which takes into account only: the total number of the parameters (a) through (e) that each simultaneously, independently exhibit at least one of the non-reassuring characteristics at the given point in time during labor, and the total number of the parameters (f) through (h) which are present; and Providing at least one display which depicts in a single graphical user interface information respecting one or more of the parameters (a) through (h) over time during labor, and the appearance of which single graphical user interface includes indicia for indicating the determined present level of risk to the fetus at any given point in time during labor and signaling the need for possible intervention in labor.

According to another feature, the invention comprehends a method for determining the present level of risk to a fetus during labor, and for displaying information related to and facilitating the identification of the level of fetal risk during labor on a single graphical user interface, the method comprising:

At the conclusion of each of a plurality of predetermined periods of time during labor, displaying on the single graphical user interface for the just-concluded period of time at least indicia corresponding to the determined present level of risk to the fetus for the just-concluded period of time;

Wherein the present level of risk to the fetus is determined from maternal uterine activity in a patient, (a) fetal heart rate ("FHR"), (b) baseline FHR variability, (c) FHR accelerations, (d) FHR decelerations, (e) maternal uterine activity, (f) maternal risk factors, (g) obstetrical risk factors, and (h) fetal risk factors distinct from the parameters (a) through (d); and Wherein the present level of risk to the fetus corresponds directly to the number of parameters (a) through (e) which simultaneously, independently exhibit at least one non-reassuring characteristic from among a plurality of pre-defined non-reassuring characteristics, and the number of parameters (f) through (h) which are present.

BRIEF DESCRIPTION OF THE DRAWINGS

The present invention will be appreciated from the following description and accompanying drawings, of which.

WRITTEN DESCRIPTION

Figure 1:
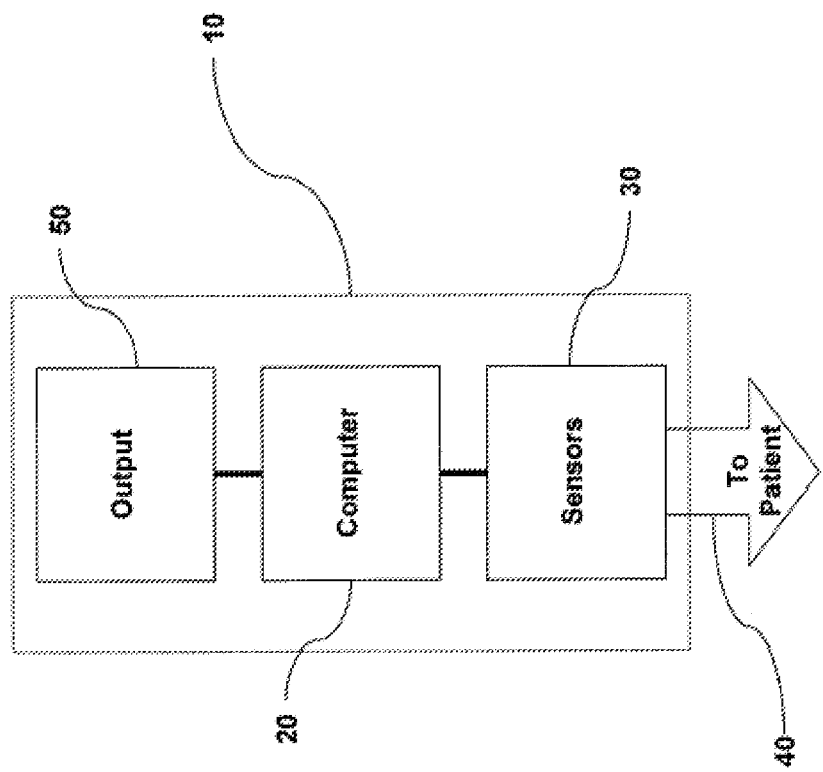
FIG. 1 is a diagrammatic depiction of an exemplary construction for an apparatus for implementing the inventive method.

As required, detailed embodiments of the present invention are disclosed herein. However, it is to be understood that the disclosed embodiments are merely exemplary of the invention that may be embodied in various and alternative forms. The accompanying drawings are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

Referring now to the drawings, there is disclosed a method and apparatus for objectively determining and identifying fetal risk during labor. The method most generally comprises the steps of monitoring a plurality of variable, dynamic parameters associated with EFM (e.g., FHR, baseline FHR variability, FHR accelerations, FHR decelerations) and maternal uterine activity (i.e., contractions), as well as taking into account certain maternal, obstetrical and fetal risks factors (separate from EFM data), to determine whether each parameter independently exhibits at least one non-reassuring characteristic/is present in a patient; and deriving an indication of the present level of risk to the fetus corresponding to the number of these parameters which simultaneously, independently exhibit at least one non-reassuring characteristic/are present. Collectively, the parameters taken into account are referred to as the "Fetal Reserve Index" ("FRI") and, according to an exemplary embodiment, comprise the following:

1. Fetal Heart Rate
2. Baseline variability
3. Accelerations
4. Decelerations
5. Uterine activity
6. Maternal risk factors
7. Obstetrical risk factors
8. Fetal risk factors (separate from EFM)

Per the exemplary embodiment, "Fetal Heart Rate" comprehends each of the "basal rate" (i.e., a normal, stable heart rate at the outset of fetal monitoring) and the "baseline rate" (i.e., the heart rate at any moment in time during the prior of labor, averaged over 20 minutes), where the non-reassuring characteristic for the baseline rate is any of a heart rate of more than 160 bpm for at least 10 minutes, a greater than 15 bpm rise over the basal rate, a heart rate of less than 110 bpm for at least 10 minutes, or a greater than 15 bpm drop below the basal rate.

Also per the exemplary embodiment, the parameters (2) through (4) are each monitored for the independent exhibition of any one or more known characteristics of non-reassurance (i.e., signs from EFM data that the fetal environment is potentially abnormal), such as, by way of non-limiting example, those set forth below:

Baseline Variability <5 bpm
FHR Non-Reactive pattern (<2 accelerations in 10 mins of Accelerations 15 bpm for 15 secs) or Absence of shoulders; or
Presence of overshoots
FHR Late decelerations; or
Decelerations Variable decelerations with slow return to baseline FHR; or
Presence of overshoots; or
Prolonged FHR deceleration Also per the exemplary embodiment, the parameter (5) (features of uterine activity) is monitored for the independent exhibition of any one or more known characteristics of non-reassurance such as, by way of non-limiting example, those set forth in TABLE 1 below.

TABLE 1

|  | Normal (20 minutes) | Abnormal |
| --- | --- | --- |
| Frequency | <=8 contractions | >8 UC (tachysystole) |
| Duration | <90 seconds | >90 seconds |
| Increased Tonus | With toco | Coupling/prolonged >120 sec |
|  | With IUPC | >20 mmHg |
| Interval A | Interval - peak to peak | <2 minutes |
| Interval B | Interval - offset of UC to onset of next UC | <1 minute |
| Rest time | >50% | <50% |

Per the exemplary embodiment, the parameter of "Maternal Risk Factors" comprises the following:
1) Decreased cardiac output/vascular perfusion of the placenta
   a. Cardiac Disease with risk of decreased cardiac output in pregnancy
   b. Hypertension (Chronic and Pregnancy induced)
   c. SLE (systemic lupus erythematosus), etc.
2) Oxygen carrying capacity
   a. Pulmonary disorders (e.g. Asthma)
   b. Anemia and Hemoglobinopathy
3) Infection (chronic and acute)
4) Chronic debilitating disease
5) Malabsorption/Poor weight gain
6) Endocrine—Diabetes and Thyroid disorders
7) Advanced maternal age
8) Drug abuse, addiction, and smoking
9) Obesity—BMI (body mass index)>35
10) Short stature (≤5'2")
11) Epidural anaesthesia Per the exemplary embodiment, the parameter of "Obstetrical Risk Factors" comprises the following:
1) IUGR (intrauterine growth restrictions)/Macrosomia
2) Oligohydramnios
3) Polyhydramnios
4) Bleeding and abruption
5) Previous cesarean section
6) Placental and umbilical cord anomalies
7) Rupture of membranes (PPROM—preterm premature rupture of membranes, SROM—spontaneous rupture of membranes, AROM—artificial rupture of membranes)
8) Dystocia (protraction and arrest disorders of labor)
9) Malpresentation Per the exemplary embodiment, the parameter of "Fetal Risk Factors" comprises the following:
1) Abnormal Dopplers/BPP (biophysical profile)
2) Genetic disorders
3) Fetal arrhythmia
4) Meconium passage
5) Chorioamnionitis
6) Second stage of labor—pushing
7) Amnioinfusion
8) Discontinuation of Pitocin due to fetal intolerance
9) Conversion patterns (acute prolonged tachycardia (>170 bpm))
10) Ominous overshoots
11) Bradycardia (<100 bpm)
12) Missing important data in labor (e.g. lack of EFM in second stage)

In one exemplary embodiment, the present invention comprehends an apparatus comprising: at least one computer operative to receive input signals indicative of at least FHR and maternal uterine activity in a patient. The at least one computer is further operative (i) to determine from the FHR at least baseline FHR variability, FHR accelerations, and FHR decelerations, and (ii) to determine when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e). The at least one computer is also operative to (iii) receive user-inputs indicative of the presence in the patient of one or more (f) maternal risk factors, (g) obstetrical risk factors, and (h) fetal risk factors distinct from the parameters (a) through (d) which elevate the level of fetal risk during labor, and (iv) to determine at a given point in time during labor a present level of risk to the fetus which takes into account only: the total number of the parameters (a) through (e) that are each simultaneously, independently exhibit at least one of the non-reassuring characteristics at the given point in time during labor, and the total number of the parameters (f) through (h) which are present.

At least one output is operatively connected to the at least one computer, the at least one output comprising a display which continuously depicts in a single graphical user interface one or more of the parameters (a) through (h) over time during labor, and the appearance of which single graphical user interface includes indicia for indicating the determined present level of risk to the fetus at any given point in time during labor. The graphical user interface includes indicia signaling the need for possible intervention in labor.

Preferably, the parameter of maternal uterine activity (e) is monitored for the exhibition of at least one non-reassuring characteristic independent of fetal response.

As exemplified herein in the described embodiments of the invention, correspondence between the number of parameters (a) through (h) that are present/simultaneously, independently exhibit at least one non-reassuring characteristic, on the one hand, and the indication of the present level of risk to the fetus, on the other hand, is preferably, though not necessarily, a one-to-one correspondence. Thus, for instance, the highest level of risk to the fetus according to the method at its most essential (i.e., monitoring the parameters (a) through (h)) corresponds to the simultaneous, independent exhibition of at least one non-reassuring characteristic for/presence in the patient of each of the parameters (a) through (h), while the lowest level of risk to the fetus corresponds to the absence of any exhibited non-reassuring characteristics for/presence in the patient of any of these parameters.

It will be appreciated that the parameters (a) through (e) discussed herein (and corresponding to the FRI parameters 1 through 5) are dynamic parameters which are subject to change in either direction (e.g., from normal, or reassuring, to abnormal, or non-reassuring, and back again) during the course of monitoring. On the other hand, the parameters (f) through (h) discussed herein (and corresponding to the FRI parameters 6 through 8) are unidirectional in nature, meaning that, once (and if) they occur (whether during the course of labor or before), they negatively affect the FRI score until delivery.

According to the present invention, at least the foregoing dynamic parameters (a) through (e) are each monitored for the independent exhibition of any one or more known characteristics of non-reassurance (i.e., signs from EFM and uterine contraction data that the fetal environment is potentially abnormal), such as, by way of non-limiting example, those identified above.

The present invention comprehends monitoring (including via conventional means) at least the specified parameters (a) through (e) for demonstration of one or more non-reassuring characteristics (such as identified herein), and further taking into account the existence or occurrence of any one or more of the unidirectional parameters (f) through (h), and indicating, in consideration of the foregoing, a present level of risk to the fetus corresponding to the number of these parameters that are simultaneously, independently non-reassuring. To this end, the invention further comprehends, according to the exemplary embodiment, a straightforward and objective system and output (e.g., graphical user interface) by which a present level of risk to the fetus is indicated, such as for the clinician, as monitoring proceeds so as to provide an indication of when intervention according to known techniques may be required, or when, in the alternative, continued observation is permissible.

The present invention further contemplates the indication of the type or types of action required for the various identified levels of risk. These types of actions are conventional in nature, as exemplified below, their performance being known to and well within the capacity of those skilled in the art. Furthermore, it will be appreciated that the types of actions specified herein are exemplary only. It is contemplated that to the extent the invention as employed provides an indication of the type or type of action required for a given level of risk, those actions may be different from those specified herein, subject only to the requirement that such actions be consistent with the interests of the patient (mother and fetus).

As further described below, the FRI score of the present invention weights various maternal, obstetrical, and fetal risk ("MOFR") factors—i.e., the unidirectional parameters—according to their anticipated effect on maternal well-being, placental and cerebral perfusion, and the probability of safe vaginal delivery. According to the exemplary embodiment more specifically, each of the eight FRI parameters (a) through (h) is assigned a "1" if the category was deemed normal (i.e., reassuring) and a "0" if abnormal (i.e., non-reassuring). The FRI score per this embodiment is calculated on the number of points divided by 8 and multiplied by 100 to give a percentage. A total of 8 parameters ((a) through (h)) being normal would result in an FRI score of 100 (8/8). A loss in points—as a function of the presence of abnormal or non-reassuring characteristics for any of the FRI parameters—would result in an FRI score of 87.5 (7/8), 75.0 (6/8), 62.5 (5/8), 50.0 (4/8), 37.5 (3/8), 25.0 (2/8), 12.5 (1/8), and 0 (0/8).

As noted above, the MOFR variables are unidirectional parameters. That is, once they occur, the reduction in point for each category remains until the fetus delivers. The EFM and excessive uterine activity (EXUA) variables, on the other hand, constitute dynamic, concurrent clinical parameters and therefore change as the characteristics of the FHR tracing change. During the course of labor, therefore, it will be understood that the FRI score may—and in most instances will—change as the dynamic, monitored parameters change and/or as unidirectional parameters may occur. The FRI score therefore represents a present indication of the level of risk to the fetus at each given point in time during labor when the score is derived.

Identification of the present level of fetal risk is made by considering each parameter (a) through (h), when present, independently from the other parameters. Thus, the schemes for identifying a present level of fetal risk that are within the scope of this invention are not, as is the case with some conventional methodologies, the consequence of interdependence between any parameters but, rather, are strictly a function of the number of parameters which are present in a patient and/or simultaneously, but independently, non-reassuring in their exhibited characteristics. Consistent with the foregoing, the inventive method is also distinguished in that it does not take into account the degree of non-reassurance indicated by the one or more characteristics of any monitored parameters. Rather, the parameters are preferably weighted equally so that any exhibition of non-reassurance according to the predetermined non-reassuring characteristic(s) for the parameters (a) through (h) will cause each such parameter to contribute equally to the presently identified level of risk.

It is also contemplated by the exemplary embodiment that the present level of risk to the fetus is identified both by a specific FRI score, as discussed above, and a grade for easy interpretation. For example, and without limitation, the "grade" of the exemplary embodiment takes the form of arbitrary color zones, akin to traffic lights. In the example of this disclosure, the lowest level of present risk to the fetus is identified as the "green zone" and comprehends FRI scores >50%. An increased (relative to the lowest level) level of present risk to the fetus is identified as the "yellow zone" and comprehends FRI scores ≤50% and >25%. The highest level of present risk to the fetus is identified as the "red zone" and comprehends FRI scores ≤25.

In the "green zone," no action is required/recommended under the exemplary scheme of the invention. In the "yellow zone," by contrast, it is recommended that the clinician's attention to the potential need for intervention in a normal vaginal delivery should be heightened. Finally, when and if the FRI score is in the "red zone," immediate resuscitation or intervention is deemed necessary according to known techniques, such as amnioinfusion, discontinuance of agents associated with uterine contractions (e.g., Pitocin, prostaglandins, etc.), or performance of operative delivery with forceps, vacuum, by cesarean section, etc.

Of course, it will be understood that the indicated type of action is intended to serve as a guideline only, and not to necessarily replace the independent judgment of the physician or other primary caregiver.

It will also be understood that there may be circumstances not expressly recited herein, and outside the scope of this invention, when the progress in labor may independently warrant intervention. Such circumstances are known to those skilled in the art.

It should be noted that calculation of the FRI as primary evaluation would, of course, be abandoned in the face of certain clinical maternal, fetal, and obstetrical events were in themselves deemed to represent sufficient, immediate indication for intervention irrespective of the other features. These included, for example, a sentinel event (uterine rupture, umbilical cord prolapse, maternal hemorrhage, etc.), and a persistent FHR bradycardia that persisted for >10 minutes—although no such examples were present in the cases.

It is contemplated that the above-specified methodology may be implemented by an apparatus 10 comprising at least one computer 20 operative to receive input signals, such as from one or more sensors 30 connected to a patient 40, indicative of at least FHR and maternal uterine activity (FIG. 1). The at least one computer 10 is operative to determine from the FHR each of baseline FHR variability, FHR accelerations, and FHR decelerations, to determine when any one or more of at least (a) FHR, (b) baseline FHR variability, (c) FHR accelerations, (d) FHR decelerations, and (e) maternal uterine activity each exhibit at least one non-reassuring characteristic (for instance, the computer may be programmed with the characteristics of non-reassurance for the aforementioned parameters, such as set forth in herein, and is operative to compare those characteristics with the input signals and determine baseline FHR variability, FHR accelerations, and FHR decelerations data), and to determine a level of risk to the fetus corresponding to the number of the parameters (a) through (e) that are simultaneously, independently non-reassuring, such as according to the scheme heretofore described. This may be accomplished by the implementation of a simple algorithm which adds the number of said parameters (a) through (e) that are simultaneously, independently non-reassuring, using arbitrarily assigned values (e.g., 1 or 0) for each.

At least one output 50 is operatively connected to the at least one computer 10 for indicating the determined present level of risk to the fetus. Operative connection of these various elements 20, 30 and 50, which may be accomplished by any known means, is indicated by bold lines in FIG. 1. The at least one output 50 may comprise, for example, a video display and/or a printer, warning lights (such as, for instance, a plurality of score-specific lights each corresponding to a different level of risk), an audible alarm, etc. It is also contemplated that the apparatus may, alternatively or in addition, be operative to provide other information, including FHR tracings, uterine activity tracings, and/or further information related to the level of risk presently indicated for the fetus, including, by way of non-limiting example, instructions to the clinician or clinicians pertaining to a predetermined action required or recommended for the identified level of risk. Such other information may be provided through the at least one output 50, for example.

The at least one computer 20 is further operative to receive user-inputs (such as via conventional means, like a keyboard, or mouse in combination with a graphical user-interface, for example) indicative of the presence in a patient of, or the occurrence during labor of, one or more of the unidirectional, MOFR parameters which elevate the level of fetal risk during labor. Alternatively, data corresponding to the unidirectional, MOFR parameters which precede presentation of the patient may be imported via a local or global computer network, such as from a patient's electronic medical records.

According to this embodiment, the at least one computer is further operative to determine, such as in the manner previously described (e.g., a simple algorithm which adds the number of said parameters using arbitrarily assigned values (e.g., 1 or 0) for each), a level of risk to the fetus corresponding to the number of the one or more unidirectional parameters (f) through (h) and the number of the said parameters (a) through (e) that are simultaneously, independently non-reassuring/abnormal.

Figure 2:
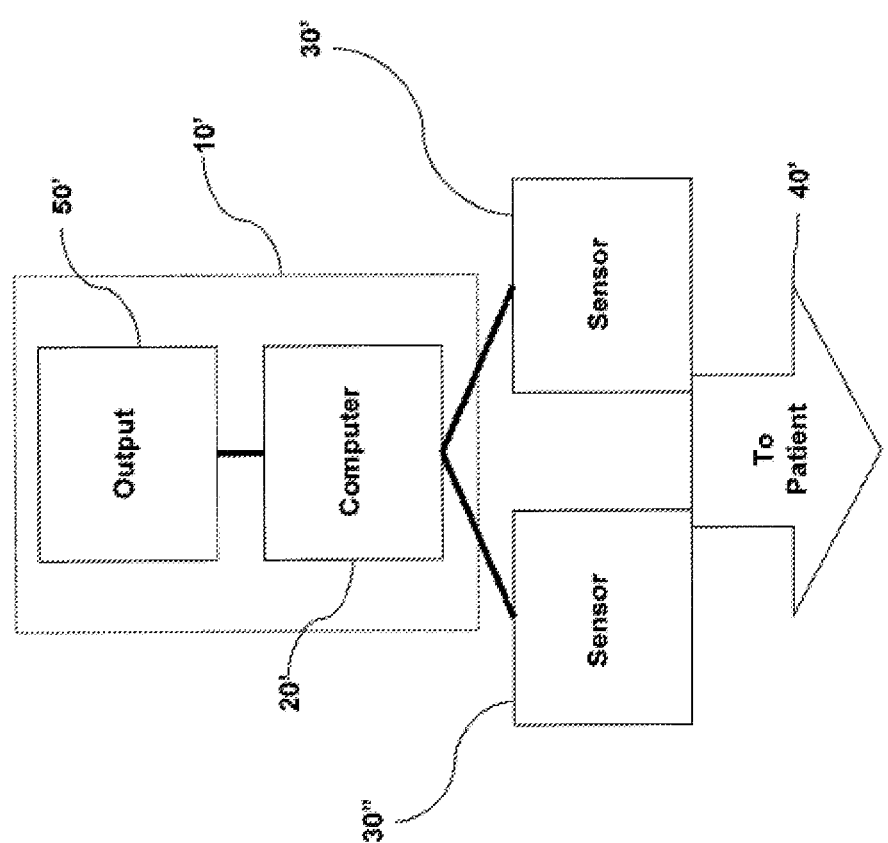
FIG. 2 is a diagrammatic depiction of a second exemplary construction for an apparatus for implementing the inventive method.

It is contemplated that the apparatus 10 may comprise a self-contained unit comprising the one or more sensors 30 capable of monitoring/receiving user-inputs indicative of the aforementioned parameters, such as shown diagrammatically in FIG. 1, or a separate unit 10' which receives inputs corresponding to these parameters from other, separate sensors 30', 30" (FIG. 2). If the former (FIG. 1), the at least one output 50 may, as noted, further be able to provide outputs including one or more of a display and/or printout showing FHR and maternal uterine contraction tracings, such as would be provided with conventional FHM and uterine contraction sensors. If the latter (FIG. 2), the apparatus for implementing the inventive methodology may be a separate apparatus connectable to a FHM device and uterine contraction sensor (each providing their own tracings) and capable of receiving data therefrom.

Figure 3:
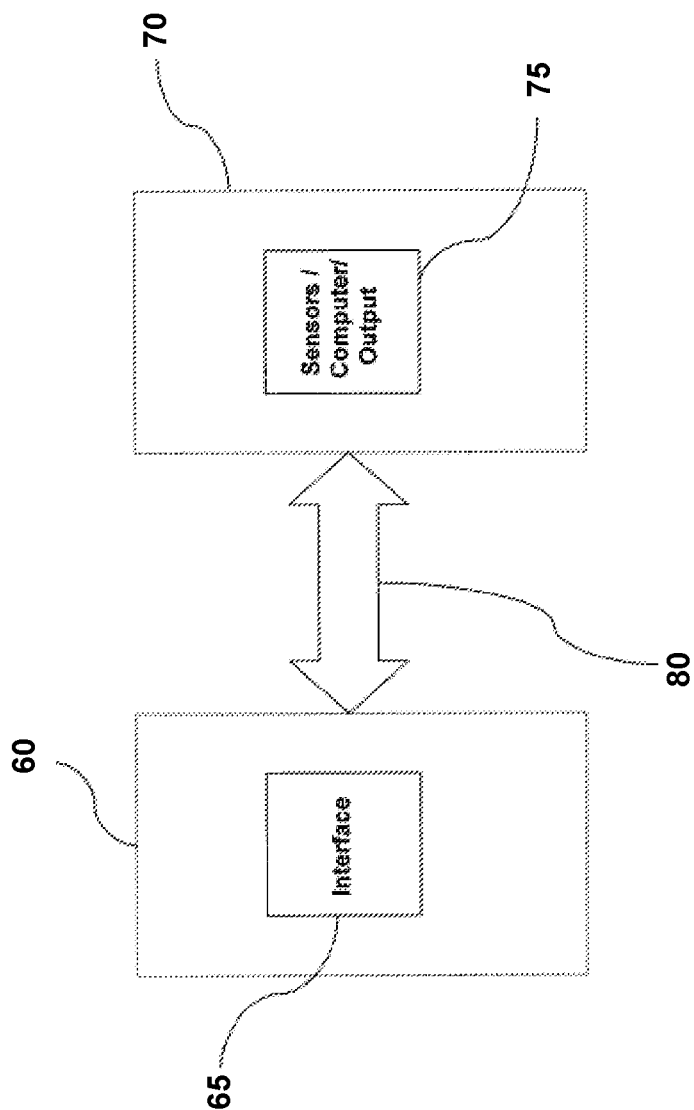
FIG. 3 is a diagrammatic depiction of an embodiment of an apparatus for implementing the inventive method providing for remote monitoring and/or feedback.

According to another embodiment of the inventive apparatus (FIG. 3), the identification of the level of fetal risk can be provided remotely, such as via the internet or other computer network (indicated at 80). According to this embodiment, it is contemplated that one or more persons, such as, for instance, one or more doctors and/or nurses in a geographically remote location 60, are provided a display/interface 65 operatively connected to the apparatus 75 at the site where the patient is located 70, such that the one or more remotely situated persons are presented with the identification of the level of risk to the fetus and, as desired, FHM and uterine contraction tracings and/or other parameters monitored so as to be capable of assisting (including via the interface and/or via other means such as a telephone, videoconference apparatus, etc.) those in the delivery room with the childbirth. For example, this system could be implemented in community hospitals lacking sufficient obstetricians in the delivery room.

In an exemplary implementation, the foregoing or other apparatus operable to perform the inventive method is operatively connected to a patient (either directly or via other monitoring apparatus) to monitor FHR and maternal uterine activity. Continuously or periodically according to a desired schedule, baseline FHR variability, FHR accelerations, and FHR decelerations are determined from the FHR and maternal uterine contraction inputs directly from the patient, and the five parameters (a) through (e) are compared against known characteristics of non-reassurance, such as those specified herein, stored in the at least one computer, to determine whether any one or more parameters independently exhibits at least one non-reassuring characteristic. When the at least one computer determines that any non-reassuring characteristics are simultaneously present for any one or more parameters (a) through (e), that determination results in an indication of the corresponding level of risk to the fetus via one or more outputs. Furthermore, the apparatus will preferably provide an indication of the action required by/recommended for the clinician or other user.

Optionally, the apparatus also would further provide for the user to specify the existence of any one or more of the unidirectional MOFR parameters occurring during the course of labor, such as via keyboard and/or mouse, via a touchscreen monitor, via dedicated input keys, etc. Each such specified parameter would, according to the exemplary scheme described above, be stored in the at least one computer and would contribute to the present level of risk determined by further adding thereto the numbers of any further dynamic parameters (a) through (e).

Experimental Results—FRI as a Reliable Identifier of Fetal Neurological Injury

To evaluate the efficacy of the methodology described above, a case control study was conducted on deliveries occurring between the years 2000 and 2013. The study represents a sample derived from 50 medico-legal consultations in babies subsequently shown to have neurological handicap. Each case was confirmed by neonatal neuroradiological examination and long-term follow up. The cases derive from diverse geographical and institutional settings in the United States ranging from small community hospitals to large metropolitan, university affiliated, and resident intensive obstetrical programs. All study patients were deemed to be at term (i.e., >36 weeks) with singleton pregnancies in vertex presentation. All had normal, reactive (i.e., reassuring) tracings at the outset of labor. Elective cesarean sections, anomalous fetuses, and those with known abnormalities (even in retrospect) were excluded from the study and control groups. In all study cases the diagnosis of long-term injury (cerebral palsy, or CP) was confirmed by neuroradiological examinations in the perinatal period and a minimum of 2 year follow-up.

The control group consisted of consecutive cases undergoing a trial of labor at term for whom FHR tracings on admission were also deemed normal and reactive.

There were no exclusions in either group for antenatal risk factors (hypertension, diabetes, etc.), nor for route, timing, or urgency of delivery. Demographic, EFM and clinical maternal, obstetrical, fetal and neonatal variables were de-identified for the analysis and, as such, qualified for exemption as evaluated by the Biomedical Research Association of NY IRB. (#16-12-180-429).

In general, no follow up examinations were deemed necessary nor performed in the control group. Normal outcome in the control group was assumed if the control newborn was discharged in a timely way, with no evidence of residual disease.

Patient data were categorized as demographic and clinical during the antepartum and intrapartum periods. Variables analyzed included standard demographics, documentation of medical, obstetrical, and fetal risk factors. Medical variables included gestational disorders (hypertension, diabetes, maternal age, BMI>40 and nulliparity) and chronic medical disorders, e.g. collagen, respiratory or cardiac. Obstetrical variables included gestational age, need for induction of labor, use of oxytocin, duration of labor (by stage), and type and urgency of delivery. Fetal factors included abnormal Dopplers/BPP, Genetic disorders, meconium, etc. These various risk factors are identified above.

Neonatal Assessment and Follow Up

Neonatal variables included standard outcome data such as birth weight, Apgar scores at 1, 5, and 10 min (when appropriate), head circumference, umbilical and neonatal pH and blood gases, neonatal adaptation, seizures, and length of stay. For cases, follow-up examinations beyond the neonatal period included type of cerebral palsy, the presence of microcephaly, hemiplegia, mental retardation, and developmental delay and seizures. Cardiac, respiratory and neurological events (seizures/coma) were recorded whether or not the newborn received cooling for neuroprotection. Acidosis was defined as per ACOG criteria as a pH<7.0/BD≥12 mEq/L in either umbilical or neonatal blood. Neonatal imaging study results were evaluated by technique (ultrasound, MRI, CAT scan) as well as the type and location of the lesions (cortical—white or gray matter, basal ganglia, stroke, other) and their symmetry. The diagnosis of hypoxic-ischemic encephalopathy (HIE) was derived from the neonatal record and related to clinical and neuroradiological findings including recent HIE (prolonged, partial, or acute), hemorrhage, and "stroke."

In this disclosure, the cases were subdivided according to the severity of both the acidosis, umbilical, and neonatal impairment. Long-term outcomes were assessed in terms of developmental delay, microcephaly, mental retardation, seizures, and problems of movement. Follow-up on study cases ranged from 2 to 16 years. Classification was attempted as to the type of cerebral palsy (e.g., spastic quadriplegia, dyskinetic CP, and hemiplegia, but classification was not productive in that these diagnoses were not consistently used in the various follow-up examinations.

In this series, no follow-up examinations were deemed necessary or performed in the control group. Such is essentially standard throughout the literature. As with virtually all studies, normal outcome in the control group were assumed if the control newborn was discharged in a timely way, with no evidence of residual disease and specifically no evidence of neonatal encephalopathy.

Assessment of FHR and Uterine Contraction Patterns

The entire FHR tracing was used to track the evolution of FHR and uterine contractions ("UC") changes from the outset of monitoring. The tracing variables included analysis of the FHR features according to standard American definitions for baseline heart rates, variability, decelerations, and accelerations (see TABLE 2A, below). Additional (non-standard) parameters include: "deceleration recovery" "data loss", "conversion pattern," and points "A" and "B" see TABLE 2A). Point "A" corresponds to the point in time in the tracing at which early deterioration (decompensation) of the fetus is occurring and that intervention is required (intrauterine resuscitation including discontinuation of Pitocin, cessation of pushing, or consideration of delivery); i.e., one can no longer be certain of the health of the fetus in the context of the estimated feasibility of safe vaginal delivery. While all point A's would be classified as American College of Obstetricians and Gynecologists ("ACOG") Category II, according to the current classifications, only a small percentage of ACOG Category II qualified as point A.

Point "B" is the pattern seen after neurological damage to the fetus has occurred. At Point "B" it is understood that neurologic damage to the fetus has occurred—irrespective of ACOG Category (II-III) or perceived presence of fetal acidemia.

The point A" and point "B" variables, while measured, were not included in the FRI score as they are qualitative in nature. They were used in the experimental results only as fixed benchmarks against which to assess the performances of screening methods and their correlation with outcomes.

For the study comprehending these results, points A and B were determined blindly.

The category "dropped data" describes as an important fetal risk factor the absence of important data during/following the deceleration or the baseline (e.g. no EFM), especially during the expulsive efforts of the 2nd stage. In some instances, this represented insertion of the maternal heart rate pattern.

TABLE 2A

Electronic Fetal Monitoring Classification

Features of Fetal Heart Rate Patterns -
Fetal Heart Rate

| | |
|---|---|
| Basal rate - | Normal, stable heart rate at the outset of monitoring |
| Baseline rate | Heart rate at any moment in time - averaged over 20 minutes - caveat |
| | Normal - Rate between 110 to 160 bpm* |
| | Abnormal - |
| | Baseline tachycardia* >160 bpm |
| | Baseline bradycardia* <110 bpm |
| *Duration at least 10 minutes | |
| | Baseline variability - variability assessed between uterine contractions and absent pushing |

| | |
|---|---|
| Normal variability - | >5 <25 bpm |
| Abnormal variability | Decreased/Absent FHR variability <5 bpm |
| | Sinusoidal, or nodal |
| | Increased FHR variability >25 bpm |
| | Accelerations - |

| | |
|---|---|
| Normal_ | At least two FHR accelerations of >15 bpm (at peak) and 15 seconds duration (from onset to offset - associated with normal baseline variability and stable baseline rate) |
| Abnormal: -- | Overshoots - increase in baseline FHR rate following contractions associated with decreased variability and absence of "shoulders". |
| Abnormal - Pathological | |
| | FHR decelerations - |

| | |
|---|---|
| Early/mild variable - | Decelerations confined to the time period of the contraction. either term suffices |
| Variable decelerations - | Abrupt decelerations >30 bpm |
| Late decelerations - | Any amplitude, but must be recurrent and proportional in amplitude and duration to the amplitude and duration of the underlying contractions |
| Prolonged decelerations - | Deceleration lasts longer than 2 min. |
| | Decelerations - "Recovery"- |

| | |
|---|---|
| Normal | Each deceleration is modified by whether or not it has "recovered", i.e., it has returned promptly to the previously normal baseline rate and variability; this must be affirmatively demonstrated; it cannot be assumed, if there are technical issues |
| Abnormal - (not recovered) | Prolonged overshoot >15 s |
| | Recovers to higher rate or increased variability |
| | Progressively rising rate until next contraction |
| | Slow return to the baseline |
| Conversion pattern - | an abrupt alteration in baseline rate and/or variability - usually in association with ongoing variable decelerations or prolonged deceleration (see examples) |
| | Dropped data - |

| | |
|---|---|
| First stage of labor | With previously normal tracing - allow 20 minutes |
| | With previously abnormal tracing - immediate evaluation and possible intervention |
| $2^{nd}$ stage of labor - | Failure to determine or establish a baseline rate immediately following deceleration × 2 is considered pathological; assigned to point A |

Specifically, neither the ACOG Category I-III system nor the 5-component Parer system was used in assessing the FRI. However, the FRI assessment was specifically compared with the ACOG categorization for all cases and controls.

Excessive uterine activity (EXUA), with its implications for uterine and fetal cerebral blood flow, was assessed according to TABLE 2B.

TABLE 2B

Features of Uterine Activity (UA)

| | Normal (20 minutes) | Abnormal |
|---|---|---|
| Frequency | <=8 contractions | >8 UC (tachysystole) |
| Duration | <90 seconds | >90 seconds |
| Increased Tonus | With toco | Coupling/prolonged >120 sec |
| | With IUPC | >20 mmHg |
| Interval A | Interval - peak to peak | <2 minutes |
| Interval B | Interval offset of UC to onset of next UC | <1 minute |
| Rest time | >50% | <50% |

For the purposes of this disclosure, the terms "hyperstimulation" and "tachysystole" are avoided as single terms to describe EXUA. The ACOG definition of tachysystole of a frequency greater than 5 contractions in 10 minutes averaged over 30 minutes speaks only to the frequency of contraction but is only one parameter in the evaluation of EXUA. Indeed, as quoted by ACOG, duration of contractions and rest time between them are important features in the analysis of contractions.

In addition, the diagnosis of EXUA should be made and responded to prior to 30 minutes as by that point there has been a significant fall in fetal oxygenation. Further, especially in the $2^{nd}$-stage 5 contractions with pushing may indeed be "excessive" for the fetus, especially if there is inadequate rest time between contractions.

Decreasing fetal reserve appears associated with greater than 4 normal contractions in 10 minutes. Importantly, it is related to diminished rest time between contractions and failure to permit fetal recovery.

Mindful of potential discrepancies in terminology, there have been assigned risk factors according to perceived abnormalities of labor using the terminology for progress in labor proposed by Friedman (arrest and protraction disorders of cervical dilatation and descent). Also, there have been added to the risk score prolongations of both the 1st and 2nd stages of labor.

Calculation of FRI

The FRI weights various maternal, obstetrical, and fetal risk ("MOFR") factors according to their anticipated effect on maternal well-being, placental and cerebral perfusion, and the probability of safe vaginal delivery.

The FRI was calculated for each 20 minute segment of monitoring. In the calculation, each of eight categories (see TABLE 3, below) is assigned a "1" if the category was deemed normal and a "0" if abnormal.

TABLE 3

COMPONENTS OF THE FETAL RESERVE INDEX

1. Fetal Heart Rate - Features
2. Baseline variability

TABLE 3-continued

COMPONENTS OF THE FETAL RESERVE INDEX

3. Accelerations
4. Decelerations
5. Uterine activity
6. Maternal risk factors
7. Obstetrical risk factors
8. Fetal risk factors (separate from EFM)

The MOFR variables are static and unidirectional; that is, once they occur, the reduction in point for each category remains until the fetus delivers. The EFM and EXUA variables, however, are dynamic and therefore change as the characteristics of the tracing changed.

The FRI was calculated on the number of points divided by 8 and multiplied by 100 to give a percentage. A total of 8 categories being normal would result in a FRI of 100 (8/8). A loss in points would result in FRI of 87.5 (7/8), 75.0 (6/8), 62.5 (5/8), 50.0 (4/8), 37.5 (3/8), 25.0 (2/8), 12.5 (1/8), and 0 (0/8).

For exemplary purposes, an abnormal FRI was defined as 25 or less (corresponding to the "red zone"—discussed further below).

In the example of these experimental results, FRI was calculated for each 20-minute segment of monitoring (EFM).

It should be noted that calculation of the FRI as primary evaluation would, of course, be abandoned in the face of certain generally accepted "sentiel" clinical maternal, fetal, and obstetrical events deemed to represent sufficient, immediate indication for intervention irrespective of the other features. These included, for example, a sentinel event (uterine rupture, umbilical cord prolapse, maternal hemorrhage, etc.), and a persistent FHR bradycardia that persisted for >10 minutes—although no such examples were present in the cases.

Time intervals were calculated for length of labor, length of 2nd stage of labor, time of first onset of abnormal FHR characteristics to delivery, point A, point B, and presence of Category III tracing. In addition, the total time (based on 20 minute segments) of each of the FHR characteristics was also analyzed. Finally, the lowest FRI score and its duration during labor, the last FRI score, and its appearance and duration of time during labor, were determined. For FRI, there is in the illustrated example both a specific score, as discussed above, and a grade for easy interpretation. For convenience, arbitrary color zones, akin to traffic lights, were created for the FRI score and plotted consecutively for each of the 20 minute segments. In the example of this disclosure, "normal" (i.e., "green zone") included FRI scores >50%, "caution" (i.e., "yellow zone") included FRI scores s50% and >25%, and "diligent" s25 (i.e., "red zone"). Time intervals from the onset of yellow and red zone to points A, B, and delivery were also analyzed, as was the total time (in 20 minute segments) of each zone during the labor (see FIGS. 4 and 5).

Conceptually, the system is such that entering the "red zone" is designed to signal the need for the presence at the bedside of senior obstetrical providers who can make decisions and implement them quickly.

Direct comparisons among the FRI, Category III ACOG tracings, and NEACP criteria were also performed with the understanding that the FRI is dependent upon FHR/uterine contraction changes as well as clinical data.

Statistical analyses were performed with independent samples t tests, $X^2$, and stepwise, logistic regression, and Levene's Test for equality of variance analyses using SPSS software.

Results

There were some statistically significant demographic differences between cases and controls which are not believed to have significantly impacted any of the main findings. The differences for FRI and outcomes between the study and control groups were so large to the point where any demographic differences could not reasonably be believed to explain any significant proportion of the variance (see TABLE 4, below). These included maternal age, proportion of nulliparas, and birth weights for which study patients were younger and closer to term which if anything would be thought to lower risk, but they were also more likely to have been induced and have heavier maternal weight which can increase risk. Many patients in both groups had multiple maternal risk factors which have not been included in previous monitor tracing interpretation.

Evaluation of the incidence of the risk factors between the cases and controls showed, not surprisingly that risk factors were more common in the case group.

Combined, overall in the cerebral palsy cases, there were an average of 4.38 risk factors/study patient versus 2.38 risk factors per control patient (NS). There were individual, significant differences such as for hypertension including pre-eclampsia (44 vs. 20%, $\chi^2$=11.1, p<0.001), morbid obesity (20 vs. 4%, $\chi$2=15.3, p<0.0001), previous cesarean section (11 vs. 6%, $\chi$2=49.2, p<0.0001), and meconium (24 vs. 7.5%, $\chi^2$=11.3, p<0.001). For most of the individual markers, the instances were low, limiting the power for statistical interpretation with this sample size. While sometimes suggestive, the numbers were too preliminary for substantive analysis. Ultimately, whatever the maternal, fetal, or obstetrical risks prevailed in each of these patients, a trial of labor was taken under by their clinicians with the expectation of vaginal delivery of a neurologically normal baby. Levene's tests were noncontributory.

There were significant differences in the various measurements of the duration and rate of progress during labor (see TABLE 4, below). The duration of both the 1st and 2nd stages of labor, the need for operative delivery, and the urgency of intervention were all greater in the case group. In addition, the indications for intervention commonly involved concern for the fetus.

There were many features of the fetal heart rate pattern that were significantly different between the study and control patients (see TABLE 5, below). All study patients reached point "A", while only 20% of the control group did. 48 of 50 study patients reached point "B." No control patient reached point "B". Of the 2 study patients in whom the timing of point "B" could not be assessed, the final tracings were actually detecting the maternal—and not the FHR—pattern (see TABLE 6, below). In a few cases, point "B" appeared after attempts at operative vaginal delivery.

Both the use of oxytocin and the appearance of excessive uterine activity were ubiquitous in the study group and common in the control group (p<0.001). Almost all cases of EXUA were associated with the use of prostaglandins or oxytocin. Diminished rest time between contractions correlated much better with adverse outcome than did frequency of contractions.

Cases had much lower 1-, 5-, and 10-min Apgar scores than controls (p<0.001). Cord gases were available in the majority of cases and were obtained in 100% of our control population. The distribution of cord gas values in the study group showed that only about 30% had pH values at or below 7.0. (TABLE 4). None of the controls did.

The vast majority of neuroradiological exams and reports describe white matter injury—so called partial, prolonged pattern involving either periventricular white matter and/or adjacent cortical gray matter injury; only about 8% had involvement of the basal ganglia, invariably in association with fetal bradycardia. About ⅓ had some evidence of intracranial or extracranial hemorrhage (the latter cases were confined to cases involving vacuum extraction). Over 80% of the fetuses suffered injury during the 2nd stage of labor, about 15% suffered injury in the latter part of the 1st stage, and 2 were injured in association with an attempted operative delivery. In these cases, the tracing reached point B only during the conduct of the vacuum or forceps. In the other 6 cases in which the vacuum was used, injury appeared during the 2nd stage of labor prior to the application of the device. The FRI score was significantly lower in study cases than in control cases both for lowest FRI, hours at the lowest FRI, and lowest FRI in the first stage (p<0.001 for all) (see TABLE 5, below). The duration of low FRI scores was much longer in cases than controls (2.2 vs 0.9 h) (p<0.001) which also resulted in a much higher incidence of operative deliveries ($\chi^2$=5.34, p<0.001).

TABLE 4

Patient Demographics and Basic Outcomes

|  | Cases | Control | t | $\chi^2$ | P< |
|---|---|---|---|---|---|
| Maternal age, years | 24.5 ± 5.4 | 27.4 ± 5.6 | 3.4 |  | 0.001 |
| Primip/Multip | 38/12 | 79/121 |  | 21.4 | 0.00001 |
| GA | 39.1 ± 1.5 | 38.1 ± 2.4 | 3.5 |  | 0.001 |
| Weight (gms) | 3438 ± 556 | 3065 ± 598 | 3.99 |  | 0.001 |
| 1 min Apgar | 3.1 ± 2.5 | 7.8 ± 1.2 | 13.2 |  | 0.001 |
| 5 min Apgar | 5.4 ± 2.8 | 8.9 ± 0.5 | 8.7 |  | 0.001 |
| pH | 7.05 ± 0.19 | 7.2 ± 0.06 | 4.3 |  | 0.001 |
| Hrs of labor | 17.7 ± 3.6 | 12.8 ± 2.5 | 4.3 |  | 0.001 |
| Induction y/n | 38/12 | 93/107 |  | 14.0 | 0.05 |
| pH <7.00 (y/n) | 8/23* | 0/200 |  | 53.4 | 0.0001 |
| + ACOG criteria (y/n) | 15/35 | 0/200 |  | 53.8 | 0.00001 |
| NEACP baby | 50/0 | 0/200 |  |  |  |

*Not available for 19 cases

TABLE 5

Fetal Reserve Index Results

|  | Cases | Controls | t | p |
|---|---|---|---|---|
| Lowest FRI score | 15 ± 4.1 | 40 ± 28.1 | 18.79 | <0.001 |
| Hours lowest FRI | 2.2 ± 1.7 | 0.9 ± 0.2 | 5.34 | <0.001 |
| Last lowest FRI | 25.5 ± 0.5 | 42.9 ± 0.4 | 7.87 | <0.001 |
| Hours Last FRI | 2 ± 1.6 | 0.9 ± 1.6 | 4.29 | <0.001 |
| FRI at end Stage 1 | 23 ± 18.3 | 62 ± 12.1 | 16.30 | <0.001 |
| $2^{nd}$ Stage hrs | 2.9 ± 1.6 | 1.0 ± 0.8 | 11.20 | <0.001 |
| $2^{nd}$ Stage 20-min segments | 5.7 ± 4.6 | 1.5 ± 2.0 | 9.12 | <0.001 |

FRI zones (colored/designated green, yellow, red in the exemplary embodiment) were used to develop predictive statistics for adverse neonatal and long-term handicap.

All study cases reached the red zone and remained there for an average of over 6 hours before delivery. By the end of the 1st stage of labor, all study patients had reached the yellow zone, and 37 (74%) had reached the red zone. At the time of delivery, 47 (94%) of study patients exceeded 2 hours in the red zone.

Graphically, it is easy to see the distinct differences in prevalence of red zone scores between the cases and controls. Representative controls and cases are graphically shown in FIGS. 4 and 5, which depict the clinical course of the first and second stages of labor, the fetal response to IR (intrauterine resuscitation), and the timing and route of delivery. In these figures, the vertical axis depicts the time to delivery (increasing from top to bottom). Each graph shows, for the given case or control, the course of labor and the "zone" (i.e., "green," "yellow" or "red") in which the FRI score fell for any given point in that course.

What these graphs illustrate is that the cases (FIG. 5) had a substantial proportion of the labor time in the red zone, whereas the controls (FIG. 4) had very little.

Figure 4:
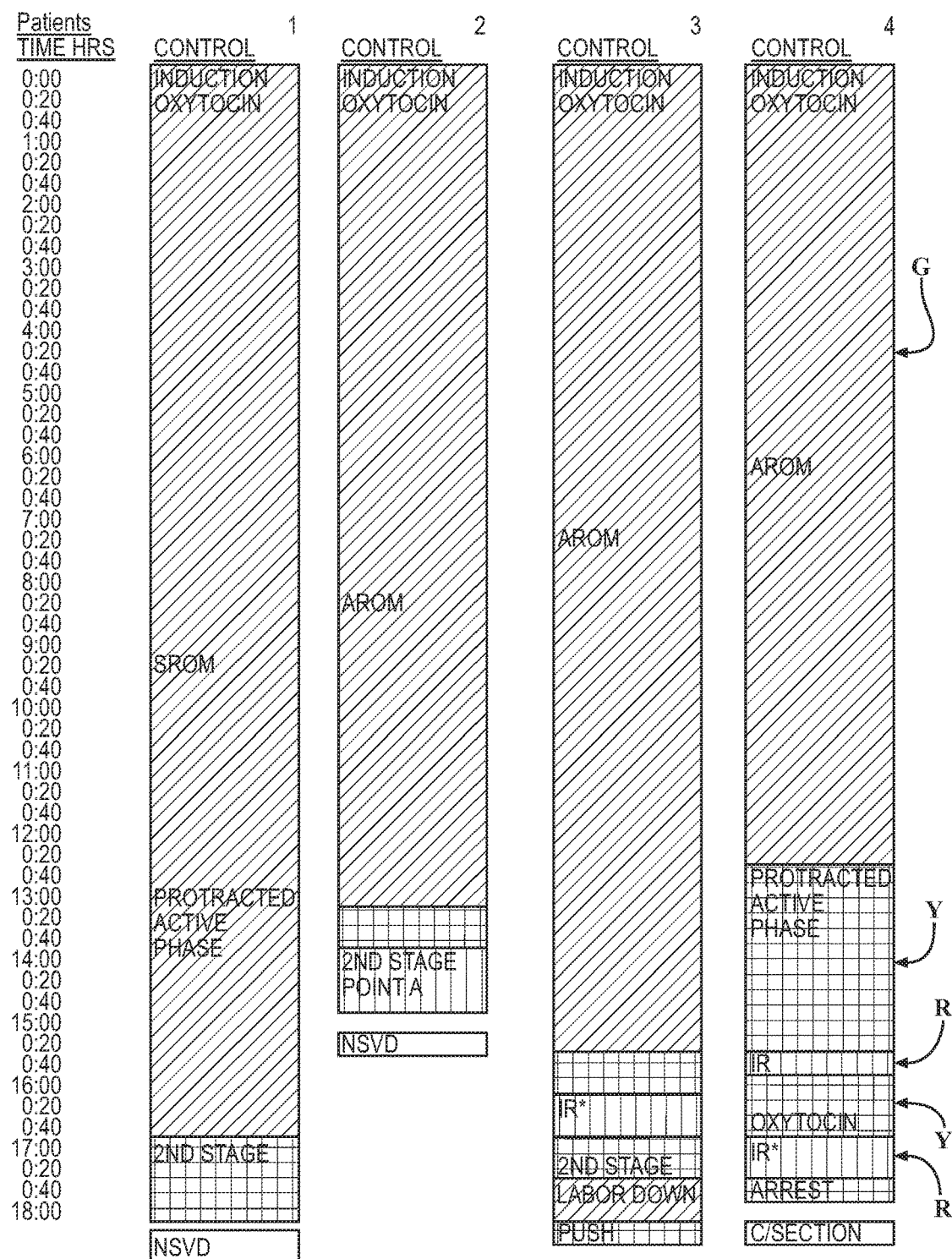
FIG. 4 is a graphical depiction of the fetal reserve index for representative control patients.
Figure 5:
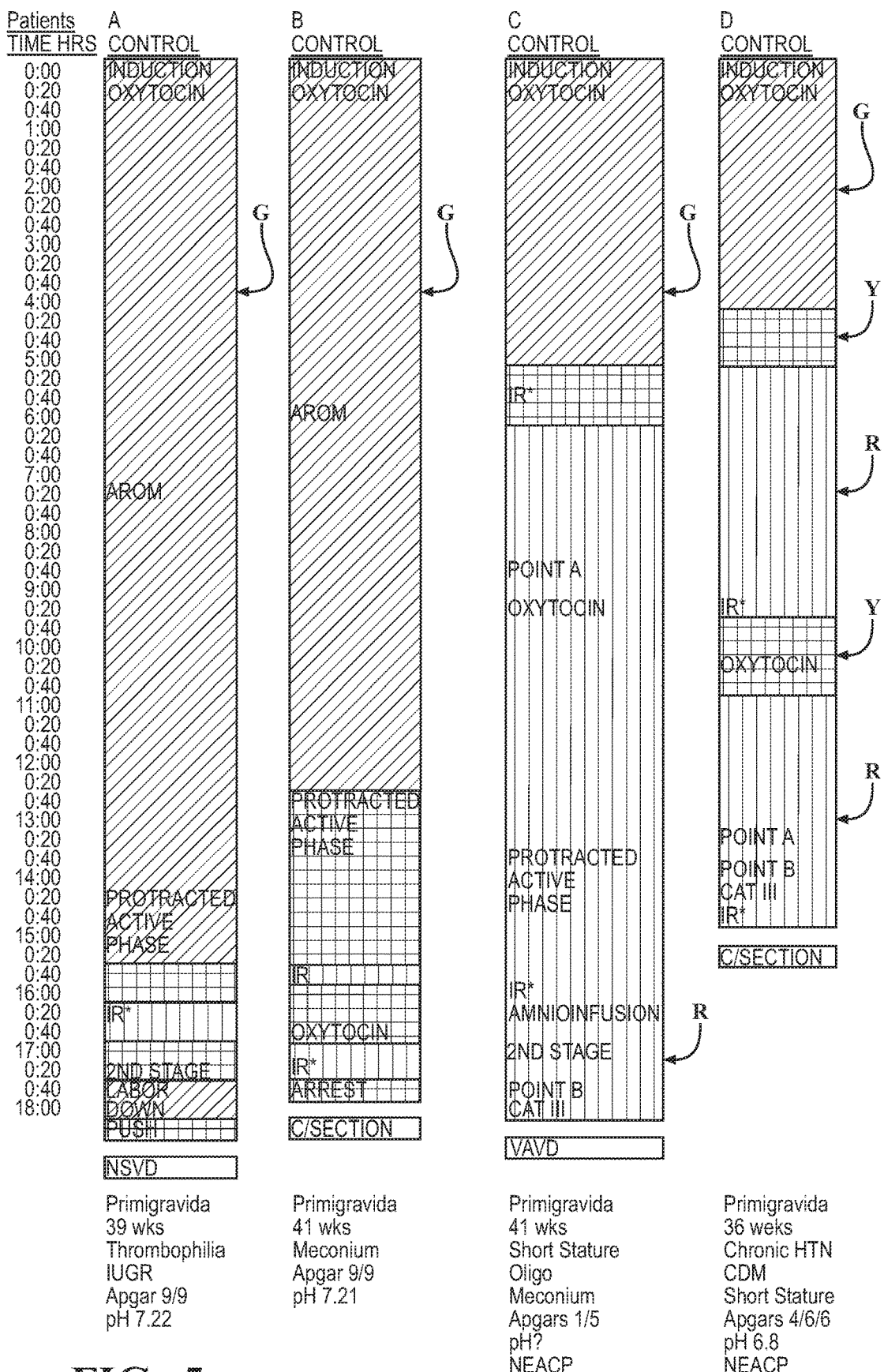
FIG. 5 is a graphical depiction of the fetal reserve index for representative cases.

The typical pattern of cases in this study was a clinical progression through the zones (green, yellow, red), then reaching point A, and point B. As shown in FIG. 4, most of the time periods are scored in the "green zone" (designated "G"), while cases 3 and 4 show reversion of "red" (designated "R") to "yellow" ("Y") following intrauterine resuscitation. In FIG. 5, the "red zone" is reached before the end of the 1st stage, and the patients remain in the "red zone" for several hours before delivery. In all 4 of these cases, the "red zone" precedes points "A" and "B," In all 4 cases, the ACOG HIE criteria were not met (pH<7.00 and Apgar at ≤5 minutes).

Conversely, in the controls only 66% reached the yellow zone, and 22% reached the red zone. Of these 37% and 10% reached the yellow and red zones respectively during the 1st stage of labor. Of those controls reaching the red zone, there was an average of 1.2 hours' duration before delivery (p<0.001). The 2nd stage seems to be a particular time of vulnerability for the fetus with as much as 80% of cases worsening significantly in the second stage (see TABLES 6 and 7, below). There was no example of reversal (improvement) of color zone designation once the patient had entered the 2nd stage, which is in part a by-product of the algorithm as points are deducted for being in the 2nd stage. However, reversal of risk strata did occur in a few control patients (see FIG. 4).

In the first stage of labor, the proportion of red zone scores was significantly different between cases and controls ($\chi^2$=93.1, p<0.00001) (see TABLE 6). The time to reach point A was less, and time from yellow to delivery was much greater for cases than controls (p<0.001). Likewise time from entrance into the red zone to delivery was much greater for cases keeping in mind that only a minority of controls got to the red zone (22%), while 37/50 (74%) of cases reached the red zone in the 1st stage versus only 20/200 of the controls (10%) ($\chi^2$=103.1 p<0.00001) (see TABLE 6).

Breaking down the components of the FRI by stepwise logistic regression, there were very significant differences between cases versus controls (see TABLE 8, below). Assessment of the individual components by stepwise logistic regression showed that abnormal variability and red zone explained the highest proportion of the variance (p<0.001) (see TABLE 9, below). Discrimination in the 2nd stage and for the lowest FRI, was even greater ($\chi^2$=117.5 and 103.7—both p<0.00001) (see TABLE 6).

TABLE 6

Fetal Reserve Index (FRI) Performance Statistics

| | CASES | CONTROLS | $\chi^2$ | p |
|---|---|---|---|---|
| $1^{ST}$ Stage Worst color | | | 103.1 | 0.00001 |
| GREEN | 0 | 125 | | |
| YELLOW | 13 | 55 | | |
| RED | 37 | 20 | | |
| $2^{ND}$ Stage Worst color | | | 117.5 | 0.00001 |
| GREEN | 0 | 17 | | |
| YELLOW | 0 | 131 | | |
| RED | 48 | 28 | | |
| Overall Worst Color | | | 103.7 | 0.00001 |
| GREEN | 0 | 16 | | |
| YELLOW | 0 | 140 | | |
| RED | 50 | 44 | | |

TABLE 7

TIME INTERVALS

| TIME (hrs) | Time, Hours CASES | Time, Hours CONTROLS | t | p | CASES | CONTROLS | X2 | P |
|---|---|---|---|---|---|---|---|---|
| Pt A to Del | 4.0 ± 2.4 | 0.6 ± 0.4 | 5.96 | 0.0001 | 50/0 | 17/183 | 170.7 | 0.00001 |
| Yellow to Del | 10.8 ± 4.6 | 2.4 ± 3.3 | 11.92 | 0.001 | | | | |
| Pt B to Del | 1.3 ± 0.8 | n.a. | | | 48/2 | 0 | 237.6 | 0.00001 |
| Pt A to Pt B | 2.7 ± 2.1 | n.a. | | | 48/2 | 0 | 237.6 | 0.00001 |
| Red to Del | 6.3 ± 3.6 | 1.2 ± 1.5 | 9.16 | 0.001 | | | | |

TABLE 8

Times to points A and B

| | TIME TO POINT A | | | | TIME TO POINT B | |
|---|---|---|---|---|---|---|
| | CASES | CONTROLS | t | p | CASES | CONTROLS |
| ABN FHR | 0.3 ± 2.3 | 0.9 ± 1.4 | 0.95 | n.s. | 3.1 | n.a. |
| ABN VAR | 6.1 ± 4.4 | 0.8 ± 1.8 | 6.81 | <0.001 | 8.6 | n.a. |
| ABSENT ACCEL | 3.7 ± 4.9 | 0.9 ± 1.6 | 3.6 | <0.001 | 6.2 | n.a. |
| ABN DECEL | 4.8 ± 4.7 | 3.2 ± 3.1 | 1.28 | n.s. | 7.6 | n.a. |
| XS UT ACTIVITY | 7.7 ± 5.2 | 6.8 ± 6.6 | 0.51 | n.s. | 10.4 | n.a |
| YELLOW | 6.9 ± 4.5 | 3.6 ± 3.8 | 2.68 | <0.009 | 9.3 | n.a. |
| RED | 2.3 ± 3.3 | 0.9 ± 1.4 | 2.37 | <0.02 | 5.1 | n.a. |

TABLE 9

Timing of abnormalities

| | CASES | CONTROLS | t | p | EQ VAR |
|---|---|---|---|---|---|
| a) TIME TO DELIVERY FROM $1^{ST}$ DIAGNOSED ABNORMALITY | | | | | |
| ABN FHR | 4.5 ± 3.2 | 1.2 ± 1.3 | 6.25 | <0.001 | N |
| ABN VARIABILITY | 10.1 ± 4.7 | 2.1 ± 3.5 | 8.92 | <0.001 | N |
| ABSENT ACCEL | 7.7 ± 5.2 | 1.2 ± 1.2 | 8.45 | <0.001 | N |
| ABN DECEL | 8.7 ± 4.9 | 2.4 ± 3.3 | 8.6 | <0.001 | N |
| XS UTERINE ACTIVITY | 11.8 ± 5.3 | 4.8 ± 4.7 | 8.78 | <0.001 | Y |
| YELLOW | 10.8 ± 4.6 | 2.4 ± 3.3 | 11.92 | <0.001 | N |
| RED | 6.3 ± 3.6 | 1.2 ± 1.5 | 9.16 | <0.001 | N |
| b) TOTAL HOURS WITH THE ABNORMALITY | | | | | |
| ABN FHR | 2.8 ± 2.0 | 0.2 ± 0.5 | 9.18 | <0.001 | N |
| ABN VARIABILITY | 8.9 ± 4.5 | 0.3 ± 1.4 | 13.24 | <0.001 | N |
| ABSENT ACCEL | 6.3 ± 3.8 | 0.2 ± 0.6 | 11.32 | <0.001 | N |
| ABN DECEL | 6.6 ± 3.4 | 1.5 ± 2.1 | 9.23 | <0.001 | N |
| XS UTERINE ACTIVITY | 9.9 ± 5.4 | 3.2 ± 3.7 | 8.28 | <0.001 | N |
| YELLOW | 5.2 ± 3.5 | 1.8 ± 2.6 | 6.48 | <0.001 | N |
| RED | 5.4 ± 2.9 | 0.2 ± 2.6 | 12.63 | <0.001 | N |
| c) RATIO HRS WITH ABN/TIME SINCE $1^{ST}$ DIAGNOSED ABNORMALITY | | | | | |
| ABN FHR | 0.75 ± 0.10 | 0.14 ± 0.03 | 11.23 | <0.001 | Y |
| ABN VARIABILITY | 0.90 ± 0.08 | 0.14 ± 0.02 | 20.9 | <0.001 | N |
| ABSENT ACCEL | 0.89 ± 0.11 | 0.17 ± 0.02 | 19.22 | <0.001 | N |
| ABN DECEL | 0.85 ± 0.12 | 0.82 ± 0.12 | 0.58 | n.s | Y |
| XS UTERINE ACTIVITY | 0.84 ± 0.15 | 0.74 ± 0.10 | 2.06 | n.s. | N |
| YELLOW | 0.50 ± 0.19 | 0.87 ± 0.14 | 3.47 | <0.001 | Y |
| RED | 0.90 ± 0.20 | 0.19 ± 0.04 | 18.34 | <0.001 | N |

Of the 50 cases of injury, only 8 cases satisfied the 2003 ACOG criteria for intrapartum injury. Extrapolating from the available clinical and neonatal findings, it is estimated that 15 cases would have met them had the data been complete. This would increase the sensitivity to 30%. By FRI, all 50 were deemed to be injured (100%). ($\chi^2$=53.8, p<0.00001) (see TABLE 10, below) Since predictive values vary with prevalence, in studies such as this in which there is an artificially increased proportion of cases to controls, the positive predictive values (PPV) must be interpreted carefully. The PPV of a "red zone" in the first stage was 65%. The negative predictive value (NPV) was 93%. Performance in the second stage and overall was even better (PPV 63%, NPV 100%) (see TABLE10).

TABLE 10

SCREENING PERFORMANCE OF METHODS

| | FRI* | Category III* | ACOG** | Point "A"* | Point "B"* |
|---|---|---|---|---|---|
| Cases/controls, n | 50/200 | 50/200 | 50/200 | 50/200 | 50/200 |
| SENSITIVITY | 100 (50/0) | 44 (22/28) | 30 (15/35) | 100 (50/0) | 96 (48/2) |
| SPECIFICITY | 78 (156/44) | 78 (156/44) | 100 (200/200) | 92 (183/200) | 100 (200/200) |
| POSITIVE PREDICTIVE VALUE*** | 53 (50/44) | 33 (22/44) | 100 (15/15) | 75 (50/67) | 100 (48/48 |
| NEGATIVE PREDICTIVE VALUE*** | 100 (156/156) | 85 (156/184) | 85 (200/235) | 100 (183/183) | 99 (200/202) |

*Prospective data

**Retrospective data

***Must be interpreted with great caution

Also evaluated was the performance of points "A" and "B." They had sensitivities the same as the FRI, and all were far higher than ACOG criteria (which is actually postnatal and not useable prospectively). The PPV of the FRI was 53%, and A was 75%. Point B was predictive of neurological handicap in 100%. By that time, however, the damage was already done although detectable prenatally for B and analyzed postnatally for ACOG (see TABLE 10).

A direct comparison was made between the FRI and ACOG Category III for detection of abnormal outcomes. The FRI (reaching the "red zone") had a sensitivity of 100% (50/50), whereas ACOG Category III had a sensitivity of 44% (22/50) ($\chi^2$=38.9, p<0.00001) (see TABLE 10). At reaching Point A, the average FRI was 16.5, reaching Point B at 3.9. For the 22/50 cases that got to ACOG Category III, the FRI was for them 1.7, consistent with a bimodal population of the parameters producing ACOG Category II. For some cases, Category III could be very sensitive, but for others it is not (similar to the mixture model in nuchal translucency screening) reducing its clinical utility as a screening test. The ACOG criteria would have only identified at most 30%, and category III only 44% of these whereas the present inventive scoring system would have picked up all 50 (100%) as being at very high risk—and did so an average of 6.3 hours before delivery, and before irrevocable damage had been done. Controls who got to the "red zone" spent only 1 hour there. Using the system of the present invention, only 17 of 200 (8.5%) controls ever got to point A, and none to point B. 48 of 50 NEACP cases got to point B and, on average, 1.3 hours prior to delivery.

Discussion

The foregoing experimental results using the FRI, which incorporates MOFR and EXUA into a modified EFM scoring system, demonstrates a sensitivity for neurological injury and subsequent handicap substantially improved over a system using the prior art ACOG Category I-III and even the retrospective ACOG NEACP monograph criteria. Prospectively, the FRI identifies patients at significant risk far earlier than Category III and avoids Category II (whose 80% incidence is much too high to be useful). The multicomponent FRI also demonstrates that combining the traditional EFM approach (with MOFR) should provide better statistical performance than EFM alone.

The results discussed herein include only patients with normal admission tracings and without suggestion of any preceding insult—even in retrospect. All cases had normal brain structure and function and were believed to have suffered injury during labor and delivery. Reasonable assurance of neurological integrity from the outset of fetal surveillance has been generally missing from studies which only consider the very last part of labor in the analysis. When such information is available, significant differences in management and conduct of labor are evident.

The ACOG criteria would have only identified (and perhaps demanded intervention in) at most 30%, and category III only 44% of these whereas the present inventive scoring system picked up all 50 (100%) as being at very high risk—and did so an average of 6.3 hours before delivery. Controls who got to the red zone had 1 hour. Only 17 of 200 (8.5%) controls ever got to point A, and none to point B. 48 of 50 NEACP cases got to point B and on average 1.3 hours prior to delivery. Injury was more often seen with Category II tracings rather than Category III.

The virtue of the FRI is that in the vast majority of cases, there is considerable cardiotocographic warning before points A and B appear and opportunity for both the avoidance of urgent intervention and the prevention of fetal injury, especially with modification of EXUA and pushing.

Conceptually, FRI provides an ongoing (not static), multiphasic, easily graphed screening test to assist the clinician in anticipating, early in the course, hypoxic/ischemic, mechanical and infectious risks to prevent fetal injury rather than tolerating getting close to the edge of some "asphyxial pattern" or labor futility before intervention. Clinical management should not be a question of "how much more can the fetus take," but the early identification of the fetus that is on a downward trajectory when potentially hostile mechanical or hypoxic features can be avoided or rectified. There would seem to be little justification for waiting until the fetus is indeed acidemic before intervening.

A second source of the misunderstanding of EFM is the role of uterine contractions, the definition of EXUA and its implications for both uterine and fetal cerebral blood flows. The commonly used ACOG definition of "tachysystole" as a single parameter seems insufficient to encompass all features of EXUA. Analysis (not shown) suggests that decreasing fetal reserve appears associated with greater than 4 normal contractions in 10 minutes, especially in the 2nd stage of labor, but importantly related to diminished rest time between contractions and the failure to permit fetal recovery.

Some contend that excessive mechanical forces are not of demonstrable harm. It seems difficult, however, to exclude a mechanical component in these previously normal, well-timed injuries in whom the majority do not meet the "essential" acid-base or Apgar score requirements of the ACOG monograph, but do undergo EXUA, prolonged labor molding and malposition and so often suffer head trauma at the time of delivery.

The FRI is based on a clinical balance by which the amount of fetal reserve (mechanical and respiratory) is judged according to the risks revealed by the FHR patterns in light of the prospects of safe vaginal delivery. The data suggest that a non-progressive labor (especially failure of descent in the 2nd stage of labor) should not be allowed solely because the EFM tracing is normal, as shorter Point A to Point B intervals tend to occur later in 2nd stage, especially when EXUA is present. Rather, the pattern of fetal descent is more important than duration. The algorithm presented here permits lengthened 2nd stages but only with progressive descent and normal FHR and uterine contraction patterns.

Further, 2nd stage risk seems increased if the 1st stage is abnormal. Entering the red zone requires the delivery team be ready and assessments made about resuscitation and delivery timing. The most important response is cessation of pushing and/or discontinuation of Pitocin—or the avoidance or EXUA and excessive pushing in the first place. Immediate resuscitative measures include temporary cessation of pushing until the fetus recovers, and delivery if IR resuscitation are ineffective.

Earlier identification of risk will initiate IR earlier when the fetus is still likely capable of recovery, and who can endure the stress of normal labor and delivery. Many of the false positive "control" cases responded well to IR and subsequently delivered vaginally without asphyxia.

Currently, all risk factors in the inventive system are weighted evenly. As data accumulate, however, the exact components and weighting of the FRI can be adapted for better statistical modeling and performance.

The system of the present invention is intended to replace very subjective and sometimes contradictory approaches of labor management with a more objective one that can be readily graphed to make it easy to follow the course of labor. The FRI parameters are quantifiable with outputs interpretable easily by clinical personnel with varying degrees of training and experience.

Experimental Results—FRI as Means of EOD Avoidance

As already noted, emergency operative deliveries (EODs), undertaken for fetal distress during labor—whether by cesarean delivery, vacuum, or forceps—increase the incidence of adverse outcomes. Despite attempts to classify cesarean deliveries according to urgency, little attention has been paid to whether or not such urgency could be moderated or even prevented.

As used herein, EOD includes at least the following:

1. Cesarean delivery for fetal intolerance of labor, including nonresponsive terminal fetal heart rate (FHR) deceleration or bradycardia and repetitive late decelerations or acute tachycardia that require emergent discontinuation of oxytocin or treatment with terbutaline (operative deliveries for arrest disorders without fetal intolerance of labor are excluded).

2. Emergency spontaneous or operative vaginal delivery preceded by fetal intolerance as mentioned earlier. Operative vaginal deliveries, either elective or for arrest disorder or maternal exhaustion, are also excluded.

3. Shoulder dystocia following an EOD that requires formal resuscitation team with performance of maneuvers such as McRoberts or supra public pressure with >1 minute total duration of maneuvers.

Notably, however, EOD excludes those patients requiring EOD shortly after admission because of manifest fetal or maternal problems, including sentinel events.

In a study population of 300 patients, all of whom had normal neonatal outcomes, the clinical course of those cases which required an EOD versus controls which did not were distinguished. Study parameters and statistical analyses were as described above in the first experimental results. The findings from this second study demonstrated that 51 cases with EOD had FRIs much lower than 249 non-EOD cases. The red zone was reached more frequently (P<0.001) and lasted longer (1.06 vs 0.05 hours; P<0.001). Reaching the red zone had a sensitivity of 92% for EOD, with a positive predictive value of 64% and a false positive rate of 10.4%.

Based on these findings, it is evident that use of the FRI scoring system of the present invention can significantly lower the incidence of EODs by identifying the opportunity for intrauterine resuscitation. The FRI can thereby serve as an effective screening test not only for fetal well-being but also for the potential need for EOD. Conceptually, the system of the present invention was designed not to see how close to a "severe" situation that could be tolerated before "rescue" but to prevent the fetus from decompensating (entering the "red zone") in the first place by scrupulous attention to the factors that compromise "reserve." To this end, there appears to be, in the previously normal fetus, a continuum of changes in the EFM tracing, from benign to ominous, which, in theory, permit early detection and prevention of both EOD and fetal harm. Thus, while preventive and resuscitative maneuvers are appropriate in the "yellow zone", having entered the "red zone", more formal responses are required, which are usually salutary, avoiding the need for immediate delivery. Importantly, entering the "red zone" signals the need for the prompt attendance, in general at the bedside, of senior obstetrical providers who can make decisions related not only to the recoverability of any abnormal FHR pattern but also assess the feasibility of safe vaginal delivery and implement them quickly to forestall fetal deterioration and avoid EOD.

Exemplary Implementation

Figure 6:
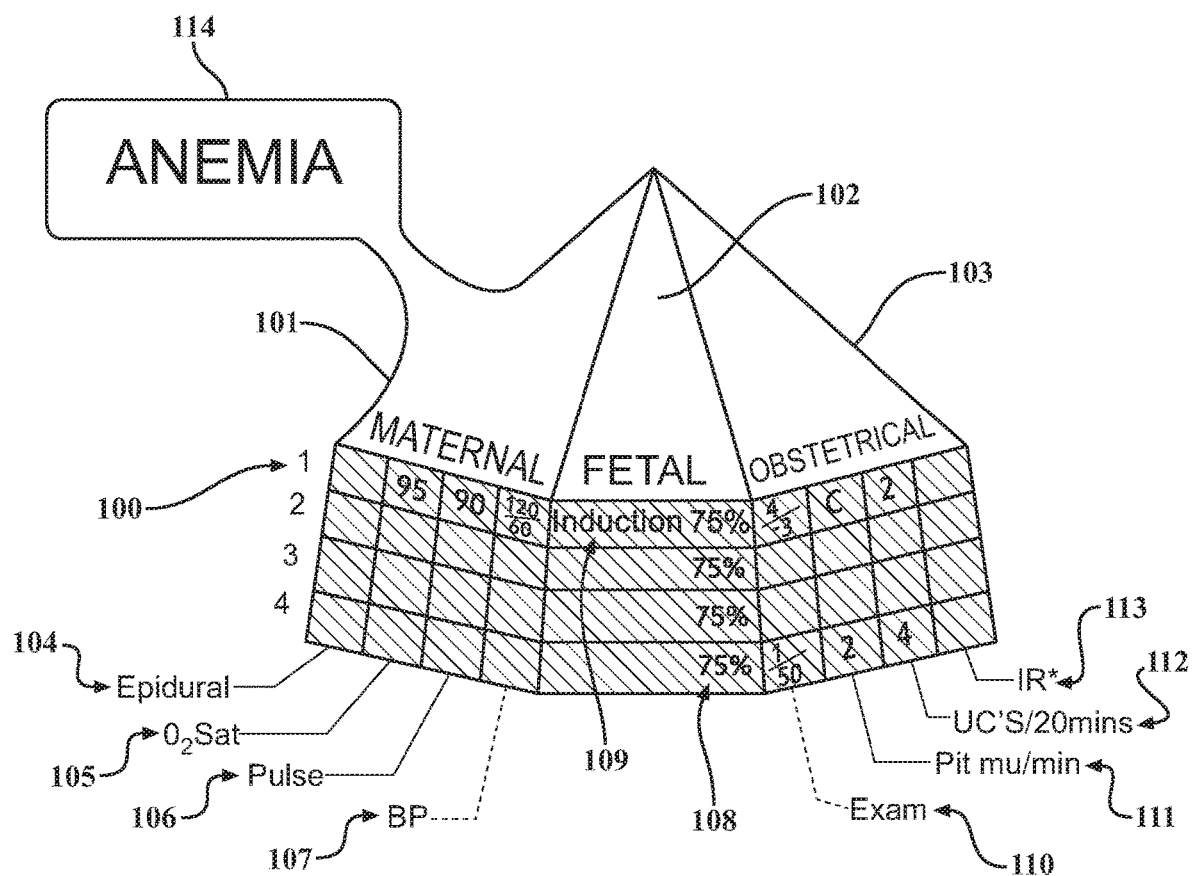
FIG. 6 is a depiction of the graphical user interface of the display depicting the display during an early stage of labor.
Figure 7:
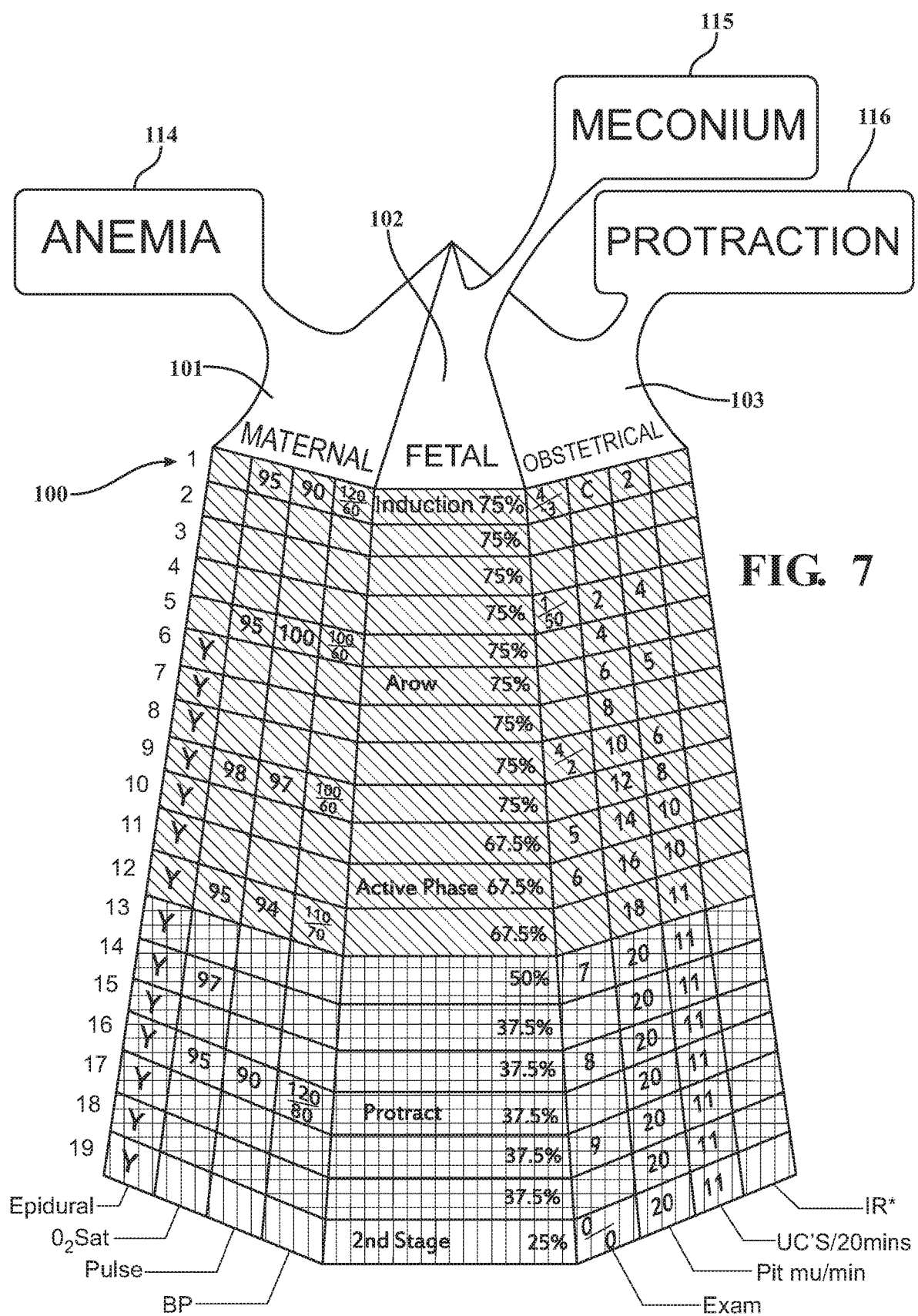
FIG. 7 is a depiction of the graphical user interface of the display depicting the display during a later stage of labor.
Figure 8:
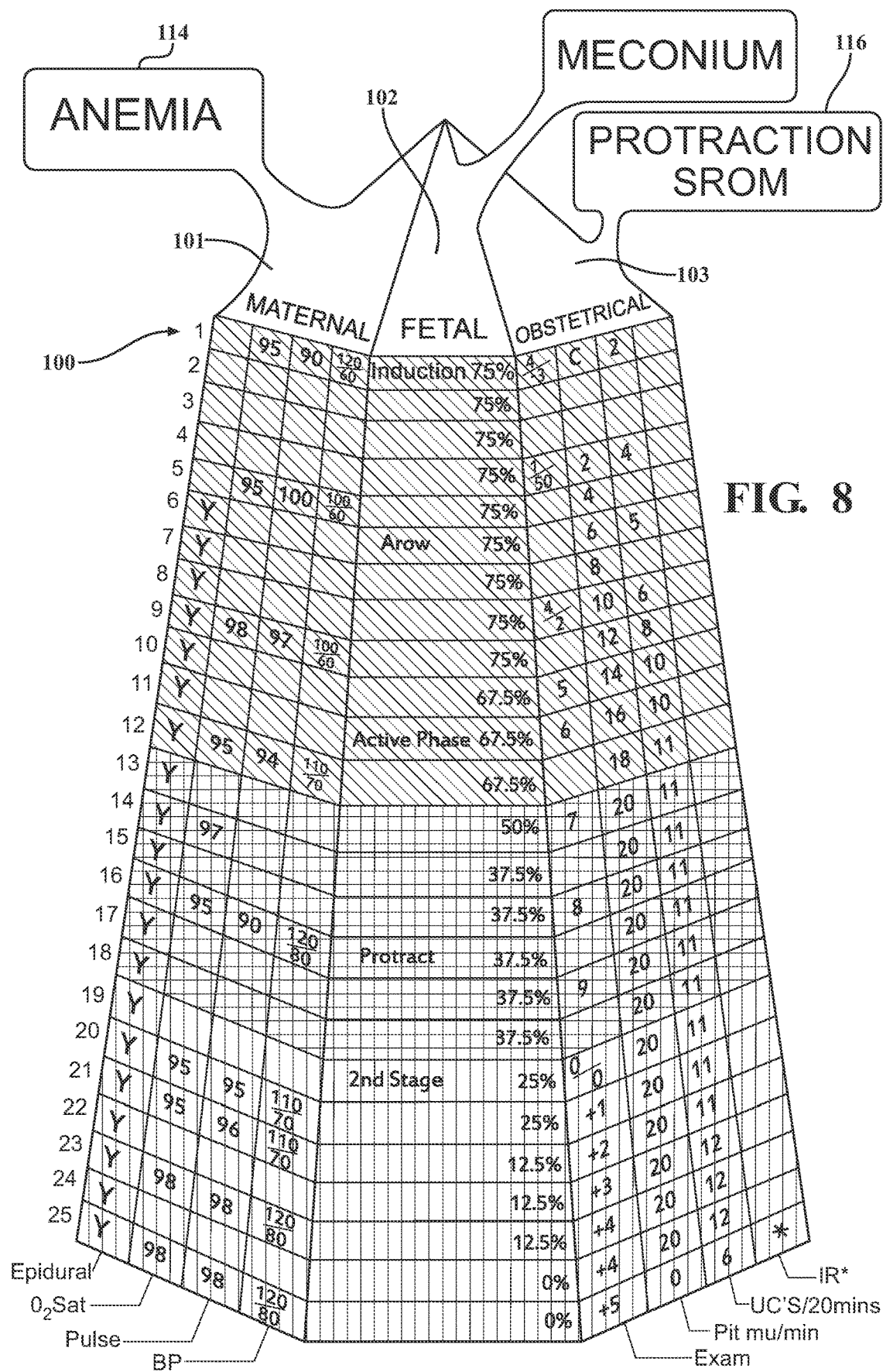
FIG. 8 is a depiction of the graphical user interface of the display depicting the display during an even later stage of labor.

Referring now to the drawings of FIGS. 6 through 8, there is shown an exemplary embodiment of a graphical user interface comprehending the system of the present invention; that is, at least one output comprising a display which continuously depicts in a single graphical user interface one or more of the dynamic and unidirectional parameters (a) through (h) over time during labor, and the appearance of which single graphical user interface includes indicia for indicating the determined present level of risk to the fetus at any given point in time during labor. Per the exemplary embodiment, the graphical user interface takes the form of a multi-faceted "obelisk" which grows over the course of labor; that is, the length of the display grows incrementally, with each added incremental row 100 representing a predefined period of labor (in the exemplary embodiment: 20 minute segments).

At the outset, the graphical user interface consists of three "denominator" components 101, 102, and 103 defining the top of the "obelisk." These components constitute the headings for relevant data displayed in the rows and column(s) immediately below each respective heading. More specifically, the component 101 denominates the "maternal" factors; component 102 denominates the "fetal" factors; and component 103 denominates the "obstetrical" factors. All of these factors and their interpretation in the system of the present invention are discussed above in greater detail.

With continuing reference to FIG. 6, the several columns comprising the "maternal" component can be seen to include one for indicating whether and when the maternal patient has been given an epidural 104, one for blood oxygen level ("02 Sat") 105, pulse 106, and one for blood pressure 107.

The column comprising the "fetal" component displays the present level of risk (shown as a percentage) to the fetus 108 and, moreover, displays relevant information respecting the course of labor. For instance, "induction" 109 is displayed in the first row (at time "1" during the first hour of labor). This information respecting the course of labor is, in the exemplary embodiment, displayed in consequence of inputs made by the physician, nurse, or other assistant, such as by inputting the information via a keyboard, via a mouse using a drop-down menu that may be incorporated into the graphical user display, etc.

The several columns comprising the "obstetrical" component 103 include one for identifying the "exam" 110, one for the rate at which Pitocin is being given to the maternal patient ("Pit mu/min") 111, one for the rate of contractions ("UC's") over a given period of time (in the illustrated example, 20 minutes) 112, and one for the occurrence of intrauterine resuscitation ("IR") 113.

With continued reference to FIG. 6, it will also be seen that, according to the illustrated embodiment, the denominator for the "maternal" factors includes a "flag" or "banner" 114 extending therefrom which reads: "ANEMIA." This "flag" 114 indicates that the maternal patient is anemic. This information respecting the course of labor is, in the exemplary embodiment, displayed in consequence of inputs made by the physician, nurse, or other assistant, such as by inputting the information via a keyboard, via a mouse using a drop-down menu that may be incorporated into the graphical user display, etc.

Further, it will be seen that the "maternal" factors denominator 101 is colored differently relative to either of the "fetal" 102 or "obstetrical" 103 denominators, reflecting the presence of the "flag" 114 as a mechanism to draw user attention to the anemic condition of the maternal patient.

It will be appreciated from the foregoing that the graphical user interface of FIG. 6 depicts the first 80 minutes of labor, as indicated by the four rows (e.g., 100) depicted beneath the denominators 101, 102, and 103. Each row is shown to be labeled with the corresponding 20-minutes segment of labor it represents; i.e., 1, 2, 3 or 4.

Finally, it may be seen that all rows (e.g., 100) below the denominators 101, 102, and 103 are similarly colored. By way of example, and without limitation, this may be the color "green," corresponding to the "green zone" discussed above. This coloring corresponds to the FRI, also discussed above. More specifically, the "green" color of the rows corresponds to the 75% results displayed below the "fetal" factors denominator 102.

Turning next to FIG. 7, there is shown the graphical user interface from FIG. 6 at a later time during delivery. More particularly, the graphical user interface is shown at 380 minutes into the progress of labor, as indicated by the 19 rows (e.g., 100) reflecting the passage of 19 20-minutes segments.

A number of things may be discerned from the graphical user interface at thisstage which reflect the progress of the exemplary labor depicted in this illustrated embodiment, including the following: First, the change in the FRI calculation: from 75% during the first 180 minutes of labor, to 67.5% during the 20-minutes segments designated by rows 10 through 12, to 50% during hour 13, to 37.5% during the period designated by rows 14 through 18, and to 25% during the latest segment (designated as row 19). Correspondingly, the rows are colored in a first color (e.g., "green") for the period of time designated by rows 1 through 12, when the FRI is above 50%; the rows are colored a second color (e.g., "yellow") for the period of time designated by rows 13 through 18, when the FRI is between 50% and 37.5%; and, finally, the last row is colored a third color (e.g. "red"), when the FRI falls below 25%. As those skilled in the art will appreciate, this coloring scheme serves to provide to physicians, nurses and other personnel a highly visible indication of the overall state of the labor corresponding to the calculated FRI and, therefore, provides an easily interpreted visual signal as to the necessity for heightened monitoring (such as when the relevant portion of the graphical user interface is colored "yellow" or another color to indicate an escalation in the assessed risk) or even intervention (such as when the relevant portion of the graphical user interface is colored "red" or another color to indicate a further escalation in the assessed risk).

Further visible in the illustrated embodiment of FIG. 7 is that the denominator for the "fetal" 102 and "obstetrical" 103 factors each include a "flag" or "banner" extending therefrom which read, respectively, "MECONIUM" 115 and "PROTRACTION" 116. The "flag" 115 indicates passage of meconium during labor (a sign of fetal distress), while the flag 116 indicates protraction of labor. The information reflected in these flags is, in the exemplary embodiment, displayed in consequence of inputs made by the physician, nurse, or other assistant, such as by inputting the information via a keyboard, via a mouse using a drop-down menu that may be incorporated into the graphical user display, etc. It will also be seen that, in consequence of the presence of these flags 115 and 116, the associated denominators 102 and 103 are colored differently than they were prior to the existence of these conditions (i.e., meconium passage and protraction). This change in color serves as an additional visual indication that a condition has arisen in the case of each denominator (i.e., the fetal and obstetrical factors) which necessitates increased attention by the physician, nurse or other assistant.

Referring to the columns below the "maternal" denominator, various entries during the temporal course of labor may be seen in the columns reflecting the maternal patient's blood oxygen level, pulse and blood pressure. It will be understood that these data may be automatically populated in the graphical user interface based on inputs from monitors connected to the maternal patient. Alternatively, or in addition, the may be manually populated by the physician, nurse or other assistant, such as via a keyboard, drop-down menu in the graphical user interface, etc. Lastly, it will be noted that the "epidural" column reflects that the maternal patient was given an epidural during the period (row 6) marking the $120^{th}$ minutes of labor.

Referring next to the column below the "fetal" denominator 102, the FRI calculation (expressed as a percentage) is displayed for each hour of labor, as mentioned. Furthermore, that column includes relevant information periodically over the displayed course of labor. Specifically, there is an entry in row 11 reflecting commencement of the "active phase" of labor, as well as an entry in row 16 indicating the onset of protraction. This information is, in the exemplary embodiment, displayed in consequence of inputs made by the physician, nurse, or other assistant, such as by inputting the information via a keyboard, via a mouse using a drop-down menu that may be incorporated into the graphical user display, etc.

Turning next to the columns below the "obstetrical" denominator 103, it will be seen that there are provided information reflecting the vaginal examination, increases in the rate of Pitocin delivery, and increases in the rate of contractions. Notably, the column reflecting intrauterine resuscitation ("IR") shows no such intervention.

With reference now being had to FIG. 8, there is shown the graphical user interface from FIGS. 6 and 7 at a later time during delivery. More particularly, the graphical user interface is shown at 500 minutes into the progress of labor, as indicated by the 25 rows (e.g., 100) reflecting the passage of 25 20-minutes increments.

A number of things may be discerned from the graphical user interface at this stage reflecting the progress of the exemplary labor depicted in this illustrated embodiment, including the following: First, the change in the FRI to 25% during the $19^{th}$ 20-minute period of labor (row 19), and progressing thereafter from 12.5% during the period represented by rows 21 to 23, to 0% during the period represented by rows 24 and 25. Correspondingly, the rows are colored in a third color (e.g., "red") for rows 19 through 25, reflecting that the FRI is at most 25% and, this, providing an easily interpreted visual signal as to the necessity for possible intervention.

Further visible in the illustrated embodiment of FIG. 8 is that the denominator 103 for the "obstetrical" factors now includes in the "flag" 116 extending therefrom the label "STROM." As noted above, this information is, in the exemplary embodiment, displayed in consequence of inputs made by the physician, nurse, or other assistant, populated manually, such as by inputting the information via a keyboard, via a mouse using a drop-down menu that may be incorporated into the graphical user display, etc.

Referring to the columns below the "maternal" denominator 101, various additional entries during the temporal course of labor may be seen in the columns reflecting the maternal patient's blood oxygen level, pulse and blood pressure. As noted above, it will be understood that these data may be automatically populated in the graphical user interface based on inputs from monitors connected to the maternal patient. Alternatively, or in addition, the may be manually populated by the physician, nurse or other assistant, such as via a keyboard, drop-down menu in the graphical user interface, etc.

Turning next to the columns below the "obstetrical" denominator 103, it will be seen that there are provided information reflecting the vaginal examination, increases in the rate of Pitocin delivery, and increases in the rate of contractions. Finally, the column reflecting intrauterine resuscitation ("IR") shows intervention (designated by an asterisk).

It will be appreciated from the foregoing disclosure that the graphical user interface and system herein disclosed may be adapted to other utilities beyond the management and monitoring of labor and delivery. For instance, and without limitation, it is contemplated that the invention herein disclosed may be adapted to: other pediatric applications, including NICU, "well-baby"/growth monitoring, HIV; surgical monitoring applications such as, for instance, anesthesia, surgical or ICU monitoring, trauma, orthopedic, urologic, vascular, ophthalmologic, ENT, podiatry, bariatric; medical/ICU applications such as medical ICU monitoring, CCU, drug abuse monitoring, neurologic monitoring, chemotherapy, hemodialysis/renal failure; chronic medical condition monitoring, such as diabetes, hyperlipidemia, endocrine disorders, general medical condition monitoring, geriatric monitoring, psychiatric monitoring, infectious disease monitoring, pulmonary disease monitoring, dermatologic condition monitoring.

By the foregoing, the invention allows for a more standardized interpretation of labor progress and FHR tracings, beneficially takes into consideration the analysis of maternal uterine activity and, optionally, maternal and fetal antecedent clinical parameters which may bear on the level of identified fetal risk during labor, and provides for the quantification of these parameters to objectively, and with consistent repeatability, identify the level of risk for the subsequent development of adverse outcomes such as fetal hypoxia and acidosis if labor is allowed to continue without intervention. Further, and as discussed above, the data suggest that the present invention can significantly lower the incidence of EODs by identifying the opportunity for intrauterine resuscitation, can reduce the disruptive effects of EODs and their concomitant increased risks of complications, and provide a metric that can refine labor management to reduce the incidents of cerebral palsy.

The foregoing description of the exemplary embodiment of the invention has been presented for purposes of illustration and description. It is not intended to be exhaustive or to limit the invention to the precise form disclosed, and modifications and variations are possible in light of the above teachings or may be acquired from practice of the innovation. The embodiments are shown and described in order to explain the principals of the innovation and its practical application to enable one skilled in the art to utilize the innovation in various embodiments and with various modifications as are suited to the particular use contemplated. Although only a few embodiments of the present innovations have been described in detail in this disclosure, those skilled in the art who review this disclosure will readily appreciate that many modifications are possible without materially departing from the novel teachings and advantages of the subject matter recited. Accordingly, all such modifications are intended to be included within the scope of the present innovations. Other substitutions, modifications, changes and omissions may be made in the design, operating conditions and arrangement of the exemplary embodiments without departing from the spirit of the present innovations.

The invention in which an exclusive property or privilege is claimed is defined as follows:

1. An apparatus for identifying the level of fetal risk during labor, the apparatus comprising:
   at least one computer operative to receive input signals indicative of at least fetal heart rate ("FHR") and maternal uterine activity in a patient, the at least one computer further operative (i) to determine from the FHR at least baseline FHR variability, FHR accelerations, and FHR decelerations, and (ii) to determine when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e);
   wherein the at least one computer is further operative to:
      (iii) receive inputs indicative of the presence in the patient of one or more parameters in the form of (f) maternal risk factors, (g) obstetrical risk factors, and (h) fetal risk factors distinct from the parameters (a) through (d) which elevate the level of fetal risk during labor; and
      (iv) to determine at predetermined points in time during labor a present level of risk to the fetus which takes into account only the total of the number of the parameters (a) through (e) that each simultaneously, independently exhibit at least one of the non-reassuring characteristics at each predetermined point in time during labor and the number of the parameters (f) through (h) which are present;
   at least one output operatively connected to the at least one computer, the at least one output comprising a display which depicts in a single graphical user interface information respecting one or more of the parameters (a) through (h) over time during labor, and the appearance of which single graphical user interface includes indicia for indicating the determined present level of risk to the fetus at the predetermined points in time during labor and signaling the need for possible intervention in labor;
   wherein the single graphical user interface displays said information over the entire period of time during which input signals indicative of at least FHR and maternal uterine activity in a patient are received by the at least one computer, which period of time continues at least to delivery; and
   said information being successively displayed as to discrete segments of time, one after the other, as the period of time during which the input signals are received increases, and said information for each discrete segment of time being persistently displayed such that the information displayed as to each discrete segment of time remains displayed in the single graphical interface as information for each successive discrete segment of time is displayed, whereby the information displayed at any given point in the period of time during which the input signals are received comprehends information for all discrete segments of time from the beginning of the period of time during which the input signals are received and continuing to the given point in time.

2. The apparatus of claim 1, wherein the highest determined level of risk to the fetus corresponds to any combination of the number of the parameters (a) through (e) that simultaneously, independently exhibit at least one non-reassuring characteristic and the number of the one or more parameters (f) through (h) which are present.

3. The apparatus of claim 1, wherein the at least one computer is further operative to identify a predetermined action to be taken in response to the indicated present level of risk to the fetus.

4. The apparatus of claim 1, wherein the maternal risk factors (f) are one or more from the group consisting of: decreased cardiac output/vascular perfusion of the placenta; diminished oxygen carrying capacity; chronic or acute infection; chronic debilitating disease; malabsorption/poor weight gain; endocrine disorders; advanced maternal age; drug abuse, drug addiction, and/or smoking; BMI >35; and a stature that is ≤5'2".

5. The apparatus of claim 1, wherein the obstetrical risk factors (g) are one or more from the group consisting of: IUGR/Macrosomia; Oligohydramnios; Polyhydramnios; Bleeding and abruption; Previous cesarean section; Placental and umbilical cord anomalies; Rupture of membranes (PPROM, SROM, AROM); Dystocia (protraction and arrest disorders of labor); and Malpresentation.

6. The apparatus of claim 1, wherein the fetal risk factors (h) are one or more from the group consisting of: Abnormal Dopplers/BPP; Genetic disorders; Fetal arrhythmia; Meconium passage; Chorioamnionitis; Second stage of labor; Amnioinfusion; Discontinuation of Pitocin due to fetal intolerance; acute prolonged tachycardia (>170 bpm); Ominous overshoots; Bradycardia (<100 bpm); lack of EFM in second stage.

7. The apparatus of claim 1, wherein the at least one non-reassuring characteristic for each of the parameters (a) through (e) is selected from the following: (a) for FHR: any of (i) a fetal heart rate of over 160 bpm or (ii) a fetal heart rate of less than 120 bpm; (b) for baseline FHR variability: any of (i) a variability of more than 15 bpm or (ii) a variability of less than 5 bpm; (c) for FHR accelerations: any of (i) the occurrence of less than two accelerations in 10 minutes of 15 bpm for at least 15 seconds, (ii) the absence of shoulders, or (iii) the presence of overshoots; (d) for FHR decelerations: any of (i) late decelerations, (ii) variable decelerations with slow return to baseline FHR, (iii) the presence of overshoots, or (iv) prolonged FHR deceleration; and (e) for maternal uterine activity: any of (i) repetitive contractions in excess of 5 uterine contractions in 3 consecutive 10 minute windows, (ii) a uterine resting tone of greater than 25 mm Hg, (iii) a contraction duration of greater than 90 seconds, (iv) the coupling or tripling of contractions prior to return to baseline, or (v) a contraction duty cycle of greater than 50%.

8. The apparatus of claim 1, wherein a highest determined level of risk to the fetus corresponds to any combination of the number of the parameters (a) through (e) that simultaneously, independently exhibit at least one non-reassuring characteristic and the number of the one or more parameters (f) through (h) which together total seven or eight.

9. The apparatus of claim 8, wherein a lowest determined level of risk to the fetus corresponds to any combination of the number of the parameters (a) through (e) that simultaneously, independently exhibit at least one non-reassuring characteristic and the number of the one or more parameters (f) through (h) which together total four or fewer.

10. The apparatus of claim 9, wherein a determined level of risk between the lowest and highest determined levels of risk to the fetus corresponds to any combination of the number of the parameters (a) through (e) that simultaneously, independently exhibit at least one non-reassuring characteristic and the number of the one or more parameters (f) through (h) which together total five or six.

11. The apparatus of claim 1, wherein the indicia signaling the need for possible intervention in labor comprise one or more colors.

12. The apparatus of claim 11, wherein the indicia signaling the need for possible intervention in labor comprise a first color when the determined level of risk is a lowest determined level of risk, a second color when the determined level of risk is between the lowest determined level of risk and a highest determined levels of risk, and a third color when the determined level of risk is the highest determined level of risk.

13. The apparatus of claim 12, wherein the graphical user interface further persistently depicts one of the first, second, or third colors for each of the said discrete segments of time.

14. A method for identifying the level of fetal risk during labor, the method comprising:
providing the apparatus as recited in claim 1;
monitoring fetal heart rate ("FHR") and maternal uterine activity in a patient;
determining via the at least one computer at least: baseline FHR variability, FHR accelerations, and FHR decelerations, and determining via the at least one computer when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e);
determining the presence in the patient of any one or more of the parameters (f)-(h);
providing to the at least one computer inputs indicative of the presence in the patient of the parameters (f)-(h) determined to be present in the patient;
determining via the at least one computer at predetermined points in time during labor a present level of risk to the fetus which takes into account only the total of the number of the parameters (a) through (e) that each simultaneously, independently exhibit at least one of the non-reassuring characteristics at each predetermined point in time during labor and of the number of the parameters (f) through (h) which are present;
providing via the at least one output a display which depicts in a single graphical user interface information respecting one or more of the parameters (a) through (h) over time during labor and continuing at least to delivery, and the appearance of which single graphical user interface includes indicia for indicating the determined present level of risk to the fetus at the predetermined points in time during labor and signaling the need for possible intervention in labor, wherein the single graphical user interface displays said information over the entire period of time during which input signals indicative of at least FHR and maternal uterine activity in a patient are received by the at least one computer; and
said information being successively displayed as to discrete segments of time, one after the other, as the period of time during which the input signals are received increases, and said information for each discrete segment of time being persistently displayed such that the information displayed as to each discrete segment of time remains displayed in the single graphical interface as information for each successive discrete segment of time is displayed, whereby the information displayed at any given point in the period of time during which the input signals are received comprehends information for all discrete segments of time from the beginning of the period of time during which the input signals are received and continuing to the given point in time.

15. The method of claim 14, wherein the highest determined level of risk to the fetus corresponds to any combination of the number of the parameters (a) through (e) that simultaneously, independently exhibit at least one non-reassuring characteristic and the number of the parameters (f) through (h) which are present.

16. The method of claim 14, wherein the at least one computer is further operative to identify a predetermined action to be taken in response to the indicated present level of risk to the fetus.

17. The method of claim 14, wherein the maternal risk factors (f) are one or more from the group consisting of: decreased cardiac output/vascular perfusion of the placenta; diminished oxygen carrying capacity; chronic or acute infection; chronic debilitating disease; malabsorption/poor weight gain; endocrine disorders; advanced maternal age; drug abuse, drug addiction, and/or smoking; BMI >35; and a stature that is ≤5'2".

18. The method of claim 14, wherein the obstetrical risk factors (g) are one or more from the group consisting of: IUGR/Macrosomia; Oligohydramnios; Polyhydramnios; Bleeding and abruption; Previous cesarean section; Placental and umbilical cord anomalies; Rupture of membranes (PPROM, SROM, AROM); Dystocia (protraction and arrest disorders of labor); and Malpresentation.

19. The method of claim 14, wherein the fetal risk factors (h) are one or more from the group consisting of: Abnormal Dopplers/BPP; Genetic disorders; Fetal arrhythmia; Meconium passage; Chorioamnionitis; Second stage of labor; Amnioinfusion; Discontinuation of Pitocin due to fetal intolerance; acute prolonged tachycardia (>170 bpm); Ominous overshoots; Bradycardia (<100 bpm); lack of EFM in second stage.

20. The method of claim 14, wherein the at least one non-reassuring characteristic for each of the parameters (a) through (e) is selected from the following: (a) for FHR: any of (i) a fetal heart rate of over 160 bpm or (ii) a fetal heart rate of less than 120 bpm; (b) for baseline FHR variability: any of (i) a variability of more than 15 bpm or (ii) a variability of less than 5 bpm; (c) for FHR accelerations: any of (i) the occurrence of less than two accelerations in 10 minutes of 15 bpm for at least 15 seconds, (ii) the absence of shoulders, or (iii) the presence of overshoots; (d) for FHR decelerations: any of (i) late decelerations, (ii) variable decelerations with slow return to baseline FHR, (iii) the presence of overshoots, or (iv) prolonged FHR deceleration; and (e) for maternal uterine activity: any of (i) repetitive contractions in excess of 5 uterine contractions in 3 consecutive 10 minute windows, (ii) a uterine resting tone of greater than 25 mm Hg, (iii) a contraction duration of greater than 90 seconds, (iv) the coupling or tripling of contractions prior to return to baseline, or (v) a contraction duty cycle of greater than 50%.

21. The method of claim 14, wherein a highest determined level of risk to the fetus corresponds to any combination of the number of the parameters (a) through (e) that simultaneously, independently exhibit at least one non-reassuring characteristic and the number of the one or more parameters (f) through (h) which together total seven or eight.

22. The method of claim 21, wherein a lowest determined level of risk to the fetus corresponds to any combination of the number of the parameters (a) through (e) that simultaneously, independently exhibit at least one non-reassuring characteristic and the number of the parameters (f) through (h) which together total four or fewer.

23. The method of claim 22, wherein a determined level of risk between the lowest and highest determined levels of risk to the fetus corresponds to any combination of the number of the parameters (a) through (e) that simultaneously, independently exhibit at least one non-reassuring characteristic and the number of the parameters (f) through (h) which together total five or six.

24. The method of claim 14, wherein the indicia signaling the need for possible intervention in labor comprise one or more colors.

25. The method of claim 24, wherein the indicia signaling the need for possible intervention in labor comprise a first color when the determined level of risk is a lowest determined level of risk, a second color when the determined level of risk is between the lowest and a highest determined levels of risk, and a third color when the determined level of risk is the highest determined level of risk.

26. The method of claim 25, wherein the graphical user interface further persistently depicts one of the first, second, or third colors for each of the said discrete segments of time.

27. The method of claim 14, wherein the step of providing an apparatus according to claim 1 further comprises that the single graphical user interface provides, for each discrete segment of time for which information is displayed, discrete areas for the display of each of maternal, fetal, and obstetrical information.

28. A method for determining the present level of risk to a fetus during labor, and for displaying information related to and facilitating the identification of the level of fetal risk during labor on a single graphical user interface, the method comprising:
providing the apparatus according to claim 1;
at the conclusion of each of a plurality of predetermined periods of time during labor and continuing at least to delivery, determining via the at least one computer the present level of risk to the fetus, and displaying on the single graphical user interface for the just-concluded period of time at least indicia corresponding to the determined present level of risk to the fetus for the just-concluded period of time, and wherein the indicia for each just-concluded period of time are successively displayed, one after the other, as the number of the plurality of predetermined periods of time increases, and wherein further the indicia for each just-concluded period of time are persistently displayed on the single graphical user interface as the number of the plurality of predetermined periods of time increases such that the indicia displayed as to each just-concluded period of time remains displayed in the single graphical interface as indicia for each successive one of the plurality of periods of time is displayed.

29. The method of claim 28, wherein the step of providing an apparatus according to claim 1 further comprises that the single graphical user interface provides, for each discrete segment of time for which information is displayed, discrete areas for the display of each of maternal, fetal, and obstetrical information.

30. The apparatus of claim 1, wherein further the single graphical user interface provides, for each discrete segment of time for which information is displayed, discrete areas for the display of each of maternal, fetal, and obstetrical information.

* * * * *